United States Patent
Denton et al.

(10) Patent No.: US 12,190,263 B2
(45) Date of Patent: Jan. 7, 2025

(54) ARTIFICIAL INTELLIGENCE BASED APPROACH FOR DYNAMIC PREDICTION OF INJURED PATIENT HEALTH-STATE

(71) Applicant: THE REGENTS OF THE UNIVERSITY OF MICHIGAN, Ann Arbor, MI (US)

(72) Inventors: Brian Denton, Ann Arbor, MI (US); Erkin Ötles, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 100 days.

(21) Appl. No.: 17/218,111

(22) Filed: Mar. 30, 2021

(65) Prior Publication Data
US 2021/0319387 A1 Oct. 14, 2021

Related U.S. Application Data

(60) Provisional application No. 63/004,357, filed on Apr. 2, 2020.

(51) Int. Cl.
*G06Q 10/0631* (2023.01)
*G06N 3/08* (2023.01)
*G16H 50/30* (2018.01)

(52) U.S. Cl.
CPC ....... *G06Q 10/063114* (2013.01); *G06N 3/08* (2013.01); *G16H 50/30* (2018.01)

(58) Field of Classification Search
CPC ........... G06Q 10/063114; G16H 50/20; G16H 50/30; G06N 3/0445; G06N 3/08; G06N 7/005
See application file for complete search history.

(56) References Cited

U.S. PATENT DOCUMENTS

| | | | |
|---|---|---|---|
| 2005/0171834 A1* | 8/2005 | Yokota | G06Q 10/00 705/7.22 |
| 2010/0131434 A1* | 5/2010 | Magent | G16H 10/60 706/14 |
| 2011/0172504 A1* | 7/2011 | Wegerich | G16H 50/30 600/301 |

(Continued)

FOREIGN PATENT DOCUMENTS

JP 6510701 B1 * 5/2019 ............. G06Q 10/10

OTHER PUBLICATIONS

"Predicting return to work after acute myocardial information", by Stendardo et al., Department of Medical Sciences, University of Ferrara, Ferrara, Italy. PLOS One, Dec. 13, 2018. (Year: 2018).*

(Continued)

*Primary Examiner* — Pan G Choy
(74) *Attorney, Agent, or Firm* — MARSHALL, GERSTEIN & BORUN LLP

(57) ABSTRACT

The following relates generally to prediction of a patient's future work-status and their Return to Work (RTW) date(s). In some embodiments, a computer-implemented method includes: training a deep learning algorithm based on (i) input observations, and (ii) work-statuses; inputting, into the deep learning algorithm, observation data of the individual patient; and predicting, with the deep learning algorithm, a work-status of the individual patient based on the observation data of the individual patient.

15 Claims, 9 Drawing Sheets

(56) References Cited

U.S. PATENT DOCUMENTS

| | | | | |
|---|---|---|---|---|
| 2012/0278100 | A1* | 11/2012 | Macoviak | G16H 80/00 |
| | | | | 705/3 |
| 2013/0024124 | A1* | 1/2013 | Collazo | G16H 50/30 |
| | | | | 702/19 |
| 2019/0027257 | A1* | 1/2019 | Ghogawala | G16H 50/70 |
| 2019/0378619 | A1* | 12/2019 | Meyer | G16H 50/70 |
| 2020/0258618 | A1* | 8/2020 | Zhou | G16H 10/60 |
| 2021/0319887 | A1* | 10/2021 | Derrick, Jr. | A61B 5/7275 |

OTHER PUBLICATIONS

Sumiyoshi et al., "Predicting work outcome in patients with schizophrenia: Influence of IQ decline", Schizophrenia Research 201 (2018), p. 172-179. (Year: 2018).*

Stendardo et al., "Predicting return to work after acute myocardial infarction", Department of Medical Sciences, University of Ferrara, Ferrara, Italy, Dec. 13, 2018. (Year: 2018).*

"Prediction of Return to Work for Patients with Low Back Pain", by Greg Mcintosh, Canadian Spine Outcomes and Research Network. Physical Therapy, vol. 77, No. 4, Apr. 2017. (Year: 2017).*

Abadi et al., "Tensorflow: Large-Scale Machine Learning on Heterogeneous Distributed Systems", arXiv:1603.04467v2 Mar. 16, 2016.

Alanazi et al., "A Critical Review for Developing Accurate and Dynamic Predictive Models Using Machine Learning Methods in Medicine and Health Care", J Med Syst, 41: 69, (2017).

Apple Inc., HealthKit Data Types, Retrieved from the Internet at: <URL:https://developer.apple.com/documentation/healthkit/data_types> (2020).

Bahdanau et al., "Neural Machine Translation by Jointly Learning to Align and Translate", arXiv:1409.0473v7, May 19, 2016.

Bai et al., "EHR Phenotyping Via Jointly Embedding Medical Concepts and Words into a Unified Vector Space", BMC Medical Informatics and Decision Making, 18(Suppl 4):123 (2018).

Baldi et al., "Hidden Markov Models of Biological Primary Sequence Information", Proceedings of the National Academy of Sciences of the United States of America, vol. 91, pp. 4059-1063, Feb. 1994.

Bartolucci et al., "Latent Markov Models for Longitudinal Data", Taylor & Francis Group, LLC, International Standard Book No. 13:978-1-4665-8371-9, (2012).

Beam et al., "Clinical Concept Embeddings Learned from Massive Sources of Medical Data", arXiv:1804.01486v3, Aug. 20, 2019.

Beck et al., "The Markov Process in Medical Prognosis", Med Decis Making, vol. 3, No. 4, p. 419-458, (1983).

Bengio et al., "Learning Long-Term Dependencies with Gradient Descent is Difficult", IEEE Transactions on Neural Networks, vol. 5, No. 2, Mar. 1994.

Boden et al., "Economic Consequences of Workplace Injuries and Illnesses: Lost Earnings and Benefit Adequacy", American Journal of Industrial Medicine, vol. 36, Iss. 5, (1999).

Boden et al., "The Impact of Non-Fatal Workplace Injuries and Illnesses on Mortality", American Journal of Industrial Medicine 59:1061-1069, (2016).

Bookstein et al., "Operations Research Applied to Document Indexing and Retrieval Decisions", Journal of the Association of Computing Machcinery, vol. 24, No. 3, p. 418-427, Jul. 1977.

Brier, Glenn W., "Verification of Forecasts Expressed in Terms of Probability," Monthly Weather Review, 78(1): p. 1-3, (1950).

Buitinck et al., "API Design for Machine Learning Software: Experiences from the Scikit-Learn Project", arXiv:1309.0238v1, Sep. 1, 2013.

Chen et al., "A Markov Chain Model Used in Analyzing Disease History Applied to a Stroke Study", Journal of Applied Statistics, 26(4): p. 413-422, (1999).

Chen et al., "xgboost: extreme Gradient Boosting", Package Version 0.6-4, p. 1-4 Jan. 4, 2017.

Cho et al., "Learning Phrase Representations using RNN Encoder-Decoder for Statistical Machine Translation," Proceedings of the 2014 Conference on Empirical Methods in Natural Language Processing (EMNLP), p. 1724-1734, Oct. 25-29, 2014.

Choi et al., "Doctor AI: Predicting Clinical Events via Recurrent Neural Networks", Proceedings of Machine Learning for Healthcare, arXiv:1511.05942v11, (2016).

Choi et al., "Using Recurrent Neural Network Models for Early Detection of Heart Failure Onset", Journal of the American Medical Informatics Association, 24(2): p. 361-370, (2017).

Christie et al., "Dynamic Multi-Outcome Prediction After Injury: Applying Adaptive Machine Learning for Precision Medicine in Trauma", PLoS One, 14(4), (2019).

Clay et al., "A Systematic Review of Early Prognostic Factors for Return to Work Following Acute Orthopaedic Trauma", Injury, 41(8): p. 787-803, (2010).

De Stavola, Bianca L., "Testing Departures from Time Homogeneity in Multistate Markov-Processes", Journal of the Royal Statistical Society Series C-Applied Statistics, 37(2): p. 242-250, (1988).

Docker Inc., Docker, Retrieved from the Internet at: <URL:https://www.docker.com> dowloaded on Jan. 23, 2022.

Dong et al., "Economic Consequences of Workplace Injuries in the United States: Findings from the National Longitudinal Survey of Youth (NLSY79)", American Journal of Industrial Medicine, 59(2): p. 106-18, (2016).

Dymarski, Przemyslaw, "Hidden Markov Models: Theory and Applications", BoD—Books on Demand, (2011).

Ervasti et al., "Prognostic Factors for Return to Work after Depression-Related Work Disability: A Systematic Review and Meta-Analysis", Journal of Psychiatric Research, 95: p. 28-36, (2017).

Franche et al., "Course, Diagnosis, and Treatment of Depressive Symptomatology in Workers Following a Workplace Injury: A Prospective Cohort Study", The Canadian Journal of Psychiatry, 54(8): p. 534-546, Aug. 2009.

Gal et al., "A Theoretically Grounded Application of Dropout in Recurrent Neural Networks", arXiv:1512.05287v5, Oct. 5, 2016.

Geron, A., "Hands-On Machine Learning with Scikit-Learn and TensorFlow: Concepts, Tools, and Techniques to Build Intelligent Systems", O'Reilly Media, Inc., (2017).

Gers et al., "Learning Precise Timing with LSTM Recurrent Networks", Journal of Machine Learning Research, vol. 3, p. 115-143, (2002).

Gers et al., "Learning to Forget: Continual Prediction with LSTM", IEEE Conference Publication, (1999).

Ghahramani, Zoubin, "An Introduction to Hidden Markov Models and Bayesian Networks", International Journal of Pattern Recognition and Artificial Intelligence, (2001).

Goodfellow et al., "Deep Learning", MIT Press, (2016).

Google, "Embeddings", Retrieved from the Internet at: <URL:https://developers.google.com/machine-learning/crash-course/embeddings/video-lecture> Last updated Jul. 18, 2022.

Google, "Word embeddings", Retrieved from the Internet at: <URL:https://www.tensorflow.org/tutorials/text/word_embeddings> Last updated Dec. 14, 2022.

Gragnano et al., "Common Psychosocial Factors Predicting Return to Work After Common Mental Disorders, Cardiovascular Diseases, and Cancers: A Review of Reviews Supporting a Cross-Disease Approach", J Occup Rehabil, 28(2): p. 215-231, (2018).

Graves et al., "Neural Turing Machines", arXiv:1410.54012v2, (2014).

Graves, A., "Supervised Sequence Labelling with Recurrent Neural Networks", Studies in Computational Intelligence, vol. 385, p. 1-141, (2012).

Green, Colin, "Cross Entropy", Retrieved from the Internet at: <URL:https://heliosphan.org/cross-entropy.html> (2016).

Greff et al., "LSTM: A Search Space Odyssey", IEEE Transactions on Neural Networks and Learning Systems, 28(10): p. 2222-2232, (2017).

Gross et al., "Development of a Computer-Based Clinical Decision Support Tool for Selecting Appropriate Rehabilitation Interventions for Injured Workers", J Occup Rehabil, 23(4): p. 597-609, (2013).

Haldorsen, E.M., "The Right Treatment to the Right Patient at the Right Time", Occupational and Envornmental Medicine, 60(4): p. 235-236, (2003).

Hochreiter et al., "Long Short-Term Memory", Neural Computation, (1997).

(56) References Cited

OTHER PUBLICATIONS

Hogg-Johnson et al., "Early Prognostic Factors for Duration on Temporary Total Benefits in the First Year Among Workers with Compensated Occupational Soft Tissue Injuries", Occupational and Environment Medicine, 60(4): p. 244-53, (2003).
Hornik, Kurt, "Multilayer Feedforward Networks Are Universal Approximators", Neural Networks, 2(5): p. 359-366, (1989).
Hou et al., "Worker's Compensation and Return-to-Work Following Orthopaedic Injury to Extremities", Journal of Rehabilitation Medicine, 40(6): p. 440-455, (2008).
Huang et al., "Probabilistic Modeling Personalized Treatment Pathways Using Electronic Health Records", Journal of Biomedical Informatics, 86: p. 33-48, (2018).
Jimmy Patronis, Florida's Chief Financial Officer, Division of Workers' Compensation, "Claims", Retrieved from the Internet at: <URL:https://dwcdataportal.fldfs.com/ClaimsDataExtract.aspx> (2021).
Jozefowicz et al., "An Empirical Exploration of Recurrent Network Architectiures", Proceedings of the 32nd International Conference on Machine Learning, (2015).
Kay, Richard, "A Markov Model for Analyzing Cancer Markers and Disease States in Survival Studies", Biometrics, 42(4): p. 855-865, (1986).
Keras, "Embedding", Retrieved from the Internet at: <URL:https://keras.io/layers/embeddings/> downloaded Jan. 2023.
Kingma et al., "Adam: A Method for Stochastic Optimization", arXiv:1412.6980v9, Jan. 30, 2017.
Lee et al., "Prediction of Return-to-Original-Work After an Industrial Accident Using Machine Learning and Comparison of Techniques", J Korean Med Sci, 33(19): p. e144, (2018).
Leigh, J. Paul, "Economic Burden of Occupational Injury and Illness in the United States", The Milbank Quarterly, 89(4): p. 728-772, Dec. 2011.
Lewis, David D., "Naive (Bayes) at Forty: The Independence Assumption in Information Retrieval", European Conference on Machine Learning, Springer, (1998).
Lurati, Ann Regina, "Health Issues and Injury Risks Associated with Prolonged Sitting and Sedentary Lifestyles", Workplace Health & Safety, 66(6): p. 285-290, (2018).
McGilchrist et al., "A Markov Transition Model in the Analysis of the Immune Response", Journal Theory Biology, 138(1): p. 17-21, (1989).
MDGuidelines, Retrieved from the Internet at: <URL:https://www.mdguidelines.com> (2023).
Meyers et al., "Applying Machine Learning to Workers' Compensation Data to Identify Industry-Specific Ergonomic and Safety Prevention Priorities", Ohio, 2001 to 2011. Journal of Occupational and Environmental Medicine, 60(1): p. 55-73, (2018).
Mikolov et al., "Recurrent Neural Network Based Language Model", Interspeech 2010.
Miller et al., "Cybernetics and Forecasting Techniques by A.G. Ivakhnenko and V.G. Lapa", Management Science Series B-Application, 15(10): p. B571-B572, (1969).
Na et al., "A Machine Learning-Based Predictive Model of Return to Work After Sick Leave", Journal of Occupational and Environmental Medicine, 61(5): p. e191-e199, 2019.
Nanda et al., "Bayesian Decision Support for Coding Occupational Injury Data", Journal of Safety Research, 57: p. 71-82, (2016).
National Safety Council, "Work Safety Introduction", Retrieved from the Internet at: <URL:https://injuryfacts.nsc.org/work/work-overview/work-safety-introduction/> (2023).
NVIDIA, "NVIDIA Container Toolkit", Retrieved from the Internet at: <URL:https://github.com/NVIDIA/nvidia-docker> (2022).
Odg by mcg, "Return-to-Work Guidelines/Modeling", Retrieved from the Internet at: <URL:https://www.mcg.com/odg/odg-solutions/return-work-guidelines-modeling> Jul. 14, 2022.
Okechukwu et al., "Marginal Structural Modelling of Associations of Occupational Injuries with Voluntary and Involuntary Job Loss Among Nursing Home Workers", Occupational and Environmental Medicine, 73(3): p. 175-82, (2016).
Olah, C., "Understanding LSTM Networks", Retrieved from the Internet at: <URL:http://colah.github.io/posts/2015-08-Understanding-LSTMs/> Aug. 27, 2015.
Oleinick et al., "Methodologic Issues in the Use of Workers' Compensation Databases for the Study of Work Injuries with Days Away from Work. I. Sensitivity of Case Ascertainment", American Journal of Industrial Medicine, 45(3): p. 260-74, (2004).
Oxenburgh et al., "The Productivity Assessment Tool: Computer-Based Cost Benefit Analysis Model for the Economic Assessment of Occupational Health and Safety Interventions in the Workplace", Journal of Safety Research, 36(3): p. 209-214, (2005).
Papic et al., "Return to Work After Lumbar Microdiscectomy—Personalizing Approach Through Predictive Modeling", Stud Health Technol Inform, 224: p. 181-183, (2016).
Pascanu et al., "On the Difficulty of Training Recurrent Neural Networks", Proceedings of the 30th International Conference on Machine Learning, arXiv:1211.5063v2 Feb. 16, 2013.
Paszke et al., "PyTorch: An Imperative Style, High-Performance Deep Learning Library", Advances in Neural Information Processing Systems, arXiv:1912.01703v1, (2019).
Patel et al., "A Machine Learning Approach to Predicting Need for Hospitalization for Pediatric Asthma Exacerbation at the Time of Emergency Department Triage", Acad Emerg Med, 25(12): p. 1463-1470, (2018).
Pedregosa et al., "Scikit-Learn: Machine Learning in Python," Journal of Machine Learning Research, 12, p. 2825-2830, (2011).
Quinlan, J.R., "Induction of Decision Trees", Machine Learning, 1(1): p. 81-106, (1986).
Rokach et al., "Data Mining with Decision Trees: Theory and Applications", World Scientific, vol. 69, (2008).
Rosenblatt, F., "The Perceptron: A Probabilistic Model for Information Storage and Organization in the Brain", Psychological Review, 65(6): p. 386-408, (1958).
Ross, Sheldon M., Chapter 1—"Introduction to Probability Theory." Introduction to Probability Models, United Kingdom Edition, Academic Press Limited, (1993).
Ross, Sheldon M., Chapter 2—"Random Variables." Introduction to Probability Models, United Kingdom Edition, Academic Press Limited, (1993).
Ross, Sheldon M., Chapter 3—"Conditional Probability and Condititional Expectaion." Introduction to Probability Models, United Kingdom Edition, Academic Press Limited, (1993).
Ross, Sheldon M., Chapter 4—"Markov Chains." Introduction to Probability Models, United Kingdom Edition, Academic Press Limited, (1993).
Ross, Sheldon M., Chapter 5—"The Exponential Distribution and the Poisson Process." Introduction to Probability Models, United Kingdom Edition, Academic Press Limited, (1993).
Ross, Sheldon M., Chapter 6—"Continuous-Time Markov Chains." Introduction to Probability Models, United Kingdom Edition, Academic Press Limited, (1993).
Ross, Sheldon M., Chapter 7—"Renewal Theory and Its Applicications." Introduction to Probability Models, United Kingdom Edition, Academic Press Limited, (1993).
Ross, Sheldon M., Chapter 8—"Queueing Theory." Introduction to Probability Models, United Kingdom Edition, Academic Press Limited, (1993).
Ross, Sheldon M., Chapter 9—"Reliability Theory." Introduction to Probability Models, United Kingdom Edition, Academic Press Limited, (1993).
Ross, Sheldon M., Chapter 10—"Brownian Motion and Stationary Processes." Introduction to Probability Models, United Kingdom Edition, Academic Press Limited, (1993).
Ross, Sheldon M., Chapter 11—"Simulation." Introduction to Probability Models, United Kingdom Edition, Academic Press Limited, (1993).
Rossum, Guido V., "Python reference manual", CS-R9525, (1995).
Schulte et al., "An Approach to Assess the Burden of Work-Related Injury, Disease, and Distress", Am J Public Health, 107(7): p. 1051-1057, (2017).
Seabury et al., "Racial And Ethnic Differences In The Frequency Of Workplace Injuries And Prevalence Of Work-Related Disability", Health Affairs (Millwood), 36(2): p. 266-273, (2017).

(56) References Cited

OTHER PUBLICATIONS

Steenstra, et al., "Predicting Time on Prolonged Benefits for Injured Workers with Acute Back Pain", J Occup Rehabil, 25(2): p. 267-278, (2015).
Tixier et al., "Application of Machine Learning to Construction Injury Prediction", Automation in Construction, 69: p. 102-114, (2016).
Tomasev et al., "A Clinically Applicable Approach to Continuous Prediction of Future Acute Kidney Injury", Nature, 572(7767): p. 116-119, (2019).
U.S. Bureau of Labor Statistics, "Injuries, Illnesses, and Fatalities", State Occupational Injuries, Illnesses, and Fatalities, Last Modified on Jan. 19, 2023.
Vallmuur et al., "Harnessing Information from Injury Narratives in the 'Big Data' Era: Understanding and Applying Machine Learning for Injury Surveillance," Inj Prev, 2016, Suppl 1: p. i34-142.
Vogel et al., "Return-To-Work Coordination Programmes for Improving Return to Work in Workers on Sick Leave," Cochrane Library, CD011618, (2017).
Westhead et al., "Hidden Markov Models", Methods in Molecular Biology 1552, J.M. Walker, (2017).
Zachary et al., "A Critical Review of Recurrent Neural Networks for Sequence Learning", arXIV:1506.00019V4, Oct. 17, 2015.
Zucchini et al., "Hidden Markov Models for Time Series: An Introduction Using R", Chapman and Hall/CRC, (2017).

\* cited by examiner

```
#import statement
from Hopper import * create hopper database
h = dbms(verbose=verbose)

#specify data tables
#and load data
table_name = "characteristics_0"
h.create_table(table_name, ["age", "sex", "eth", "bin_ldc", "job"], ["real",
"bin", "ldc", "ldc"])
h.csv_to_table(table_name, "data/characteristics_0.csv", delimiter=',')

table_name = "samples_0"
h.create_table(table_name, ["SBP", "DBP", "type"], ["real", "real", "ldc"],
has_times=True)
h.csv_to_table(table_name, "data/samples_0.csv", delimiter=',')

table_name = "samples_1"
h.create_table(table_name,
    ["tmps", "hrs", "sbps", "rrs", "dbps", "sats", "wgts"],
    ["real", "real", "real", "real", "real", "real", "real"],
    has_times=True)
h.csv_to_table(table_name, "data/samples_1.csv", delimiter=',')

table_name = "samples_2"
h.create_table(table_name, ["dx"], ["hdc"], has_times=True)
h.csv_to_table(table_name, "data/samples_2.csv", delimiter=',')
```

FIG. 6A

```
#set sample windows for several patients, everyone else gets the default
#default is the whole time horizon
h.set_windows([['00000', 2, 5], ['00001', 3, 7]],)

#partition the dataset based on patients
#the patients specified go into the specified partitions
#everyone else gets split automatically based on 80/10/10 train/dev/test
h.set_partitions([['00000', 'dev'], ['00001', 'dev']])

#remove out of window data and split into partitions
h.create_windows_views()
h.create_partition_views_prior_to_filter()

#fit the filter on train data
#remove data that is seen 5% of the time
h.fit_filter(partition='train', percentile_cutoff=0.05)

#map the patient data to a relative calendar (t -> t~)
h.set_relcal()

#aggregate the data to days
h.fil_agg()

#parition and create a normalization based on the train set
h.create_partition_views_prior_to_normalization()
h.fit_normalization(partition='train')
```

FIG. 6B

ARTIFICIAL INTELLIGENCE BASED APPROACH FOR DYNAMIC PREDICTION OF INJURED PATIENT HEALTH-STATE

CROSS-REFERENCE TO RELATED APPLICATION

This Application claims the benefit of U.S. Provisional Application 63/004,357 filed on Apr. 2, 2020, the entirety of which is incorporated herein by reference in its entirety.

BACKGROUND

Occupational injuries cause an immense burden on the U.S. population and economy. For example, in 2016, 4.5 million people were injured in the U.S. and yearly costs to the U.S. economy were estimated to be between $150 and $250 billion. While occupational injuries (OI) vary greatly in severity, they can cause great pain and suffering. Over 30% of OIs will cause time away from work. They also disproportionately affect under-represented minorities and lead to shortened lifespans. OIs financially impact individuals, directly by causing income reduction, and indirectly by leading to job loss and increasing medical expenditures. Moreover, time away from work can have an economic impact on firms due to reduced productivity.

The following discloses improved systems and methods for dynamic prediction of return to work for injured patients.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect, there is a computer-implemented method for predicting a work-status of an individual patient, the method comprising, via one or more processors: training a machine learning algorithm based on: (i) input observations, and (ii) work-statuses; inputting, into the machine learning algorithm, observation data of the individual patient; and predicting, with the machine learning algorithm, a work-status of the individual patient based on the observation data of the individual patient.

In another aspect, there is a computer system for predicting a work-status of an individual patient, the computer system comprising one or more processors configured to: train a machine learning algorithm based on: (i) input observations, and (ii) work-statuses; input, into the machine learning algorithm, observation data of the individual patient; and predict, with the machine learning algorithm, the work-status of the individual patient based on the observation data of the individual patient.

In yet another aspect, there is a computer device for predicting a work-status of an individual patient, the computer device comprising: one or more processors; and one or more memories coupled to the one or more processors; the one or more memories including computer executable instructions stored therein that, when executed by the one or more processors, cause the one or more processors to: train a machine learning algorithm based on: (i) input observations, and (ii) work-statuses; input, into the machine learning algorithm, observation data of the individual patient; and predict, with the machine learning algorithm, a work-status of the individual patient based on the observation data of the individual patient.

In some embodiments, the work-status is a return to work (RTW) status.

The systems and methods disclosed herein advantageously improve upon prior RTW prediction systems. For example, the systems and methods disclosed herein include ways to dynamically update patient's information, which continuously improves RTW prediction. In another example, prior systems had not applied Artificial Intelligence (AI) to RTW prediction. Further advantages will be recognized by the following disclosure.

BRIEF DESCRIPTION OF THE DRAWINGS

FIGS. 6A and 6B show an example code of a data transformation pipeline.

DETAILED DESCRIPTION

Figure 1:
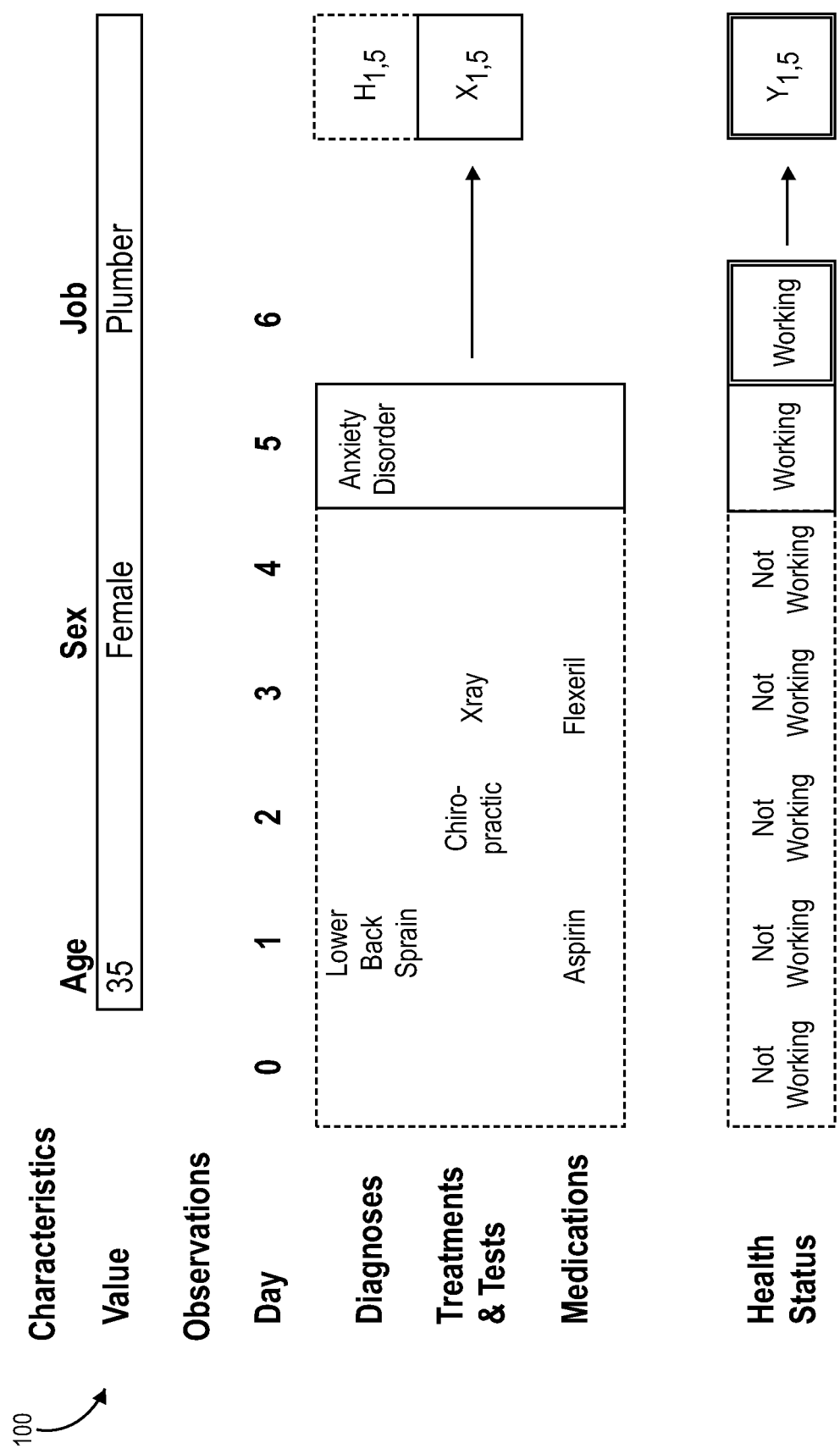
FIG. 1 illustrates an exemplary timeline demonstrating the trajectory of a simulated patient.

The present embodiments relate to, inter alia, prediction of a patient's work-status and their Return to Work (RTW). In some embodiments, the RTW is predicted as a RTW date. In other embodiments, the RTW is predicted as a work health-state at a particular time; in some implementations, the work health-state is binary (e.g., either the patient is able to work or not).

0. ABSTRACT

Physicians and payers managing the recovery of patients suffering from occupational injuries have to manage large amounts of longitudinal (temporal) data. This disclosure proposes a new framework for dynamic prediction of work-status and return to work, that yields daily predictions for the future work-status of patient's given new information, utilizing a combination of deep learning and a novel data transformation pipeline. In tandem, these methods allow for prediction of patient outcomes with respect to complex clinical information observed over time. In some example implementations, prediction experiments were conducted on a large claims dataset, covering over 1.2 million patient injuries, with good out-of-sample discriminative performance (area under the receiver operator characteristics curve example results shown in FIG. 3A) and calibration (example results shown in FIG. 3B). The following will demonstrate that it is possible to use widely available data to predict return to work, allowing physicians and payers to manage large populations of injured patients more efficiently.

1. INTRODUCTION

Managing the recovery process of injured patients is a difficult task; it involves synthesizing clinical knowledge and practice guidelines with evolving patient recovery information. This process is intense, requiring medical management by highly trained clinicians, including physicians directly guiding patient care and case managers who oversee thousands of simultaneous cases on behalf of healthcare payers. The current state of the art for patient recovery prediction are static models that are used at the onset of injury. These models are often used by payers to estimate a patient's Return to Work (RTW) date. The current static models estimate RTW based on information at the time of a patient's initial injury. Thus, providing guidance on the expected amount of resources needed for a patient's recovery, and enabling stratification of the injured patient population. While these static models may provide useful insight into initial severity and potential future resource needs, these estimates rapidly lose value as time progresses.

Over time, information regarding a patient's severity of injury, medical management, and response to treatment are revealed. Models that respond dynamically to this information may yield more accurate recovery predictions and could enhance the decision-making abilities of payers and physicians. The following proposes a new framework for dynamic prediction of RTW that yields daily predictions for the work-status of patients given new information. Some approaches disclosed herein use deep learning. By employing this model, clinicians and payers would have the opportunity to use RTW outcome estimates that are updated daily in the management of their patients recovering from OIs.

Figure 7:
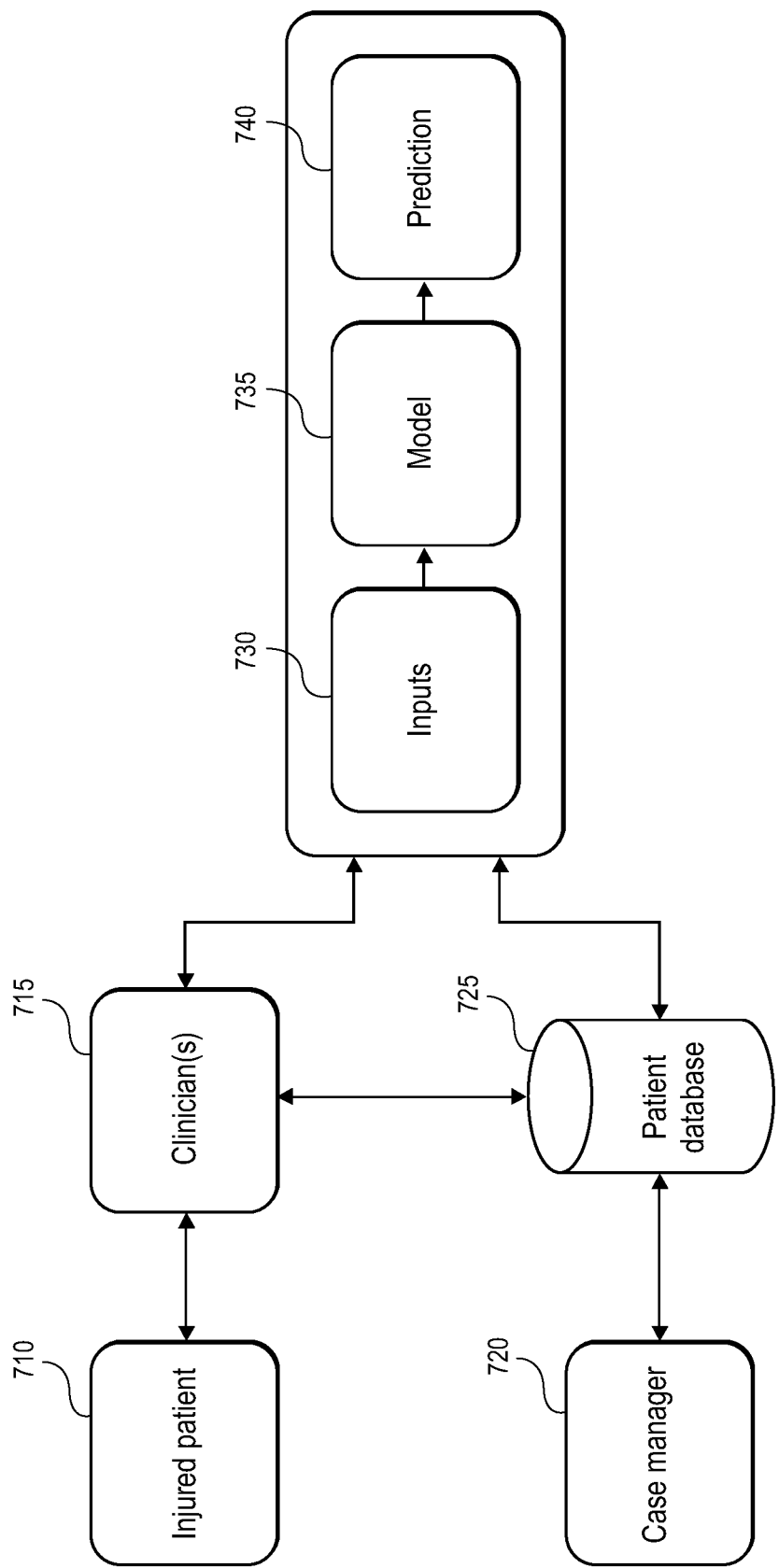
FIG. 7 illustrates an overview of an example embodiment.

FIG. 7 shows an overview of an example embodiment. With reference thereto, some embodiments build a dynamic model of a patient's 710 health-state following an OI using deep learning techniques. This dynamic health-state model 735 synthesizes the patient's 710 entire injury and treatment history (e.g., using inputs 730), and is used to make an effective and accurate prediction 740. Contextualizing the model 735 against all observed historical patient histories allows users to estimate the future work-status of a patient, which can be interpreted as the probability of a given patient returning to work. In the aggregate, such estimates for panels of patients overseen by clinicians 715 can help direct limited resources to patients at greatest risk of protracted recovery. The estimates (along with any other data) may be stored in patient database 725, and accessed by case manager 720.

1.1 Organization

The following disclosure is organized in the following sections. Section 2 presents a literature review, where related work is described in the context of OIs and cover state of the art for dynamic predictive modeling. Section 3 discloses a methodological approach and the mathematical formulation of the disclosed deep learning model. Section 4 discusses results for the disclosed model's performance based on a case study of OIs based on a large database with demographic and claims data for a population of injured workers. Section 5 summarizes the disclosed findings and opportunities for future research. Finally, Section 6 summarizes the most important conclusions from the disclosed study.

2. LITERATURE REVIEW

This literature review includes two major sections. The first section focuses on the existing state of the art for RTW modeling in the context of occupational injuries. The second section briefly summarizes the novel contributions of this this disclosure relative to existing literature.

2.1 Return to Work Literature

This section has three subsections. The first subsection provides background on factors affecting RTW for patients who experience an OI. The second subsection reviews the literature on models for quantifying decisions in the context of RTW. The last subsection summarizes potential opportunities for future work in RTW prediction.

2.1.1 Factors Affecting Return to Work

As mentioned above, every year in the United States OIs affect millions of patients and cost workplaces and payers hundreds of billions of dollars. The true burden of these injuries is likely to be significantly underestimated. In addition to physical symptoms, patients with OIs often experience complicating psycho-social issues, such as depression; however, these complicating issues are rarely detected or treated. Together, these factors provide an incentive for patients, workplaces, physicians, and payers to understand the amount of time a patient will be away from work, with the goal to eventually help minimize it.

There have been many retrospective studies that seek to identify factors affecting time of RTW. Major groups of factors include patient specific, injury related, professional, workplace related, treatment, and psycho-social factors. Examples of specific factors in each of these groups are shown in table 1 below. Predictors of shortened RTW duration include job control, work ability, perceived (good) health, and high socio-economic status. Some of the predictors of lengthened RTW duration include job strain, anxiety & depression, comorbidities, older age, and low education.

TABLE 1

Factor groups and specific factors that are related to RTW duration.

| Factor Group | Patient Specific | Injury Related | Professional | Workplace Related | Treatment | Psycho-social |
|---|---|---|---|---|---|---|
| Specific Examples | Age, Functional status, Medical comorbidities | Injury severity, Body region affected, Amount of hospitalization, Work ability | Level of education, Type of work, Union membership, Compensation | Workplace arrangements, Physical demands, Perception of injury relatedness to work, Job control, Job strain | Opioid prescriptions | Self-efficacy, Recovery-expectations, Mental health comorbidities (anxiety & depression), Perceived health, Socio-economic status |

These studies provide a view into how RTW is shaped by a combination of factors that vary across patients, workplaces, and injuries. However, the findings from these studies cannot be easily generalized across large populations of injured patients. Issues include a specific focus on subpopulations, such as patients who experience a lumbar disc herniation. [see, e.g., Papic, M., et al., Return to Work After Lumbar Microdiscectomy—Personalizing Approach Through Predictive Modeling. Stud Health Technol Inform, 2016. 224: p. 181-3.] Some of these studies also have conflicting findings, one notable example is that of the efficacy of RTW coordination programs. Specific companies may experience benefits with a coordination program, but when these programs are studied on a larger scale, through meta-analysis, there is no significant benefit when compared to standard of care. [see, e.g., Vogel, N., et al., *Return-to-work coordination programmes for improving return to work in workers on sick leave*. Cochrane Database Syst Rev, 2017. 3: p. CD011618; and Lee, J. and H. R. Kim, *Prediction of Return-to-original-work after an Industrial Accident Using Machine Learning and Comparison of Techniques*. J Korean Med Sci, 2018. 33(19): p. e144.] The last significant issue is the use of specially collected data. Many of the variables in Table 1 must be collected from patients, providers, or work-places with special research workflows.

2.1.2 Modeling Return to Work

RTW modeling has traditionally taken the form of a time-to-event prediction task. Much of the modelling work that has been done in this field treats RTW as a single event, whose occurrence time is predicted when a patient is initially injured. The most prevalent modelling technique used for this approach is the Cox proportional hazards model. There have been examples of time to RTW prediction using hazard models, with extensions to predict length receiving benefits, and prolonged claim identification. [see, e.g., Hou, W. H., et al., *Worker's compensation and return-to-work following orthopaedic injury to extremities*. J Rehabil Med, 2008. 40(6): p. 440-5; Hogg-Johnson, S. and D. C. Cole, *Early prognostic factors for duration on temporary total benefits in the first year among workers with compensated occupational soft tissue injuries*. Occup Environ Med, 2003. 60(4): p. 244-53; Steenstra, I. A., et al., *Predicting time on prolonged benefits for injured workers with acute back pain*. J Occup Rehabil, 2015. 25(2): p. 267-78; and Haldorsen, E. M., *The right treatment to the right patient at the right time*. Occup Environ Med, 2003. 60(4): p. 235-6.]

Machine learning (ML) techniques, such as decision trees, Naïve Bayes, and gradient boosted machines, have been applied to situations involving OIs other than predicting RTW. They are not routinely used for prediction of RTW, which is dominated by the time-to-event approach, and the major ML work is focused on ancillary prediction tasks. Two examples include appropriate rehabilitation intervention selection and classification of a patient's final work-state disposition. [Gross, D. P., et al., *Development of a computer-based clinical decision support tool for selecting appropriate rehabilitation interventions for injured workers*. J Occup Rehabil, 2013. 23(4): p. 597-609; Na, K. S. and E. Kim, *A Machine Learning-Based Predictive Model of Return to Work After Sick Leave*. J Occup Environ Med, 2019. 61(5): p. e191-e199]

Even though artificial intelligence is not utilized for RTW prediction, it has seen increased usage in the greater field of occupational injuries, specifically for use in automated injury coding. For example, machine learning models have been used in the context of construction related injuries to automatically retrieve injury etiology from free-text reports. These types of models have the potential to: augment human-based injury surveillance systems; classify injuries and intervention categories; and guide prevention efforts and policy.

2.1.3 Opportunities in RTW Prediction

From this existing literature, it is important to note that the state of the art in RTW prediction has several potential avenues for further exploration. The first is that models are generally made for specific diseases with custom collected data. The second is that RTW models are normally based on static time-to-event prediction, designed for usage only at time of injury, and incapable of handling newly observed information.

Modeling specific injuries through custom research databases helps physicians to refine their understanding of patient injury physiology and recovery; however, it limits the overall utility of models. The following seeks to build a model that can be used for the multitude of occupational injuries that patients experience, so some embodiments must employ a dataset that is representative of this variety. This dataset must be relatively universal in terms of its availability and its representation of patient injuries and recoveries. Statewide administrative databases of workers compensation claims represent a potential avenue for accessible and routinely collected data regarding patient injuries. For example, Gross et al.'s work on ML assisted rehabilitation intervention selection was trained with data from an administrative database. [Gross, D. P., et al., *Development of a computer-based clinical decision support tool for selecting appropriate rehabilitation interventions for injured workers*. J Occup Rehabil, 2013. 23(4): p. 597-609.] These databases have been shown to have high concordance with BLS occupational injury statistics, and thus are an excellent source of high-quality large-scale data.

RTW duration predictions made at the time of patient's injury are useful for patients, workplaces, physicians, and payers. This information helps set expectations for patients and allows workplaces to plan. Similarly, it helps physicians and payers categorize patients and plan for eventual resource usage. However, the value of this information degrades over time. Plans made with initial predictions must be updated without the guidance of validated models and there are no tools to directly compare the trajectory of current patients to historical patients.

These issues could be alleviated with the assistance of RTW prediction models that update dynamically, or over time. Traditional barriers to creating dynamic models for patient conditions have included small data-set sizes, methodologic constraints, and insufficient hardware; however, these constraints have recently been overcome. Recently, several related dynamic prediction models have been published helping physicians to screen for traumatic brain injuries, assess risk factors for recovery from non-work-related injury, and predict the need for hospitalization in pediatric asthma exacerbations. One notable recent project is a study conducted by the GOOGLE Deep Mind Health team. This team created a model to dynamically predict acute kidney injury in hospitalized patients, which was published in Nature. [Tomasev, N., et al., *A clinically applicable approach to continuous prediction of future acute kidney injury*. Nature, 2019. 572(7767): p. 116-119.]

2.2 Dynamic Prediction Methods

This section explores methodologic approaches that could be used to build dynamic prediction models for RTW. The following briefly covers the general objective of formulating RTW as a dynamic prediction task, and the following then covers two major methods used for dynamic predictions: Markov chains and deep learning.

2.2.1 Dynamic Prediction of RTW

Some embodiments disclosed herein seek to present a new approach to modeling RTW prediction, one that can be used dynamically, unlike the static time to event prediction methods, which have been the industry standard. This involves moving from a framework that treats the input and outcome as fixed, to a framework that treats the input as a sequence of information and the output as another, related sequence of information. The input sequence can be thought of as the sequence of all the collected data, or observations of a patient. And the output sequence can take several forms, either directly predicting the time-to-event of RTW, or indirectly predicting RTW by estimating probabilities of work-status at future time points. Thus, there are two sequences; and the desired task is to sequentially predict the outcome sequence given the observation sequence, a sequence-to-sequence prediction task.

2.2.2 Markov Chains

Markov chains are a well-studied and pervasive modeling technique for dynamic sequences. A Markov Chain is a stochastic process that enforces a conditional distribution between the current state $X_t$ and the future state $X_{t+1}$. A key constraint is that given a current state ($X_t$), the next state ($X_{t+1}$) is independent of all the previous states ($X_0, X_1, \ldots, X_{t-1}$), meaning that future states are only dependent on the current state.

Markov models are widely used in medicine, due to their simple structure and ease of clinical interpretability. They have been used to model prognosis, immune response, future health-status for patients with cancer. They have also been used to uncover the relationship between biomarkers and health outcomes and to analyze the histories of patients with strokes. A notable extension of the Markov chain is that of the Hidden Markov Model (HMM), which enables modeling of a sequence of observed signals while the actual sequence underlying the Markov chain is unobserved. HMMs are frequently used to study sequences generated from systems with stochasticity, and they have been used throughout the field of medicine from studying protein sequences, to analyzing human movement, and even predicting treatment decisions.

Despite their wide use, Markov chain based models are limited by their underlying formulation, which restricts the sequential dependence of ($X_{t+1}$) to only ($X_t$). More complicated processes (such as depending on the previous 3 time-steps) can be transformed into a Markov chain formulation by redefinition of the states. Thus, fixed length histories can be embedded into the current state, which allows for representation of history by state-space expansion. However, this comes at the expense of a much larger state-space. Another common assumption in Markov chain based models is time-homogeneity, as the probability of transitioning to ($X_{t+1}$) depends only on ($X_t$), independent of the current time-step, unless this dependence is represented in the state-space.

The observations for patients returning to work are high dimensional, as they include several types of categorical variables that may take on many possible values. An example of this is diagnosis, where there are thousands of possible diagnoses for patients injured at work, and on any given day a patient may have zero, one, or more diagnosis codes assigned to them. Treatment is another high-dimensional category. The timing and order of treatments may impact the recovery of an injured patient; thus, the history beyond the current observation is important in modeling RTW. This high-dimensionality and history dependence makes Markov chain based models ill-suited for the task at hand. Dimensionality could be reduced by either restricting the problem definition to a specific disease (e.g. lower back sprain) or by lowering the dimensionality by grouping. However, both of these require significant effort to create and validate specialized models. In contrast, this disclosure focuses on a generalizable approach that applies to a broad range of injuries.

2.2.3 Deep Learning Approaches

Deep learning methods have gained popularity in recent years due to improved hardware performance, the ubiquity of large datasets, and the availability of high-quality deep learning frameworks, such as TensorFlow and PyTorch. The following section discusses two deep learning approaches, feedforward neural networks and recurrent neural networks, and finishes with a discussion of important related deep learning techniques.

2.2.3.1 Feedforward Neural Networks

Feedforward neural networks (FNNs) are perhaps the simplest deep learning architecture. FNNs are straightforward extensions of the perceptron and single layer neural network, both invented in the 1960s. Instead of having a single layer, FNNs are neural networks that contain 2 or more layers—this additional "depth" is what gives deep learning its name. FNNs, like all other neural networks, can theoretically approximate any function given the right data and training environment. Because of their structure, which maps inputs to outputs through a series of layers, FNNs can be used to mimic the functionality of a Markov chain based model. The input can be a fixed length of history for a given time-step and the output can be the state (or outcome) expected at the next time-step.

FNNs can be combined with some of the approaches discussed at the end of this section in order to overcome the curse of dimensionality that affects Markov chain based models. Despite these augmentations, FNNs cannot overcome the history independence issue. In order to address this issue, some embodiments disclosed herein turn attention to Recurrent Neural Networks.

2.2.3.2 Recurrent Neural Networks

Recurrent neural network (RNNs) are a type of network learning model that have the ability to selectively store information in a hidden state vector. Unlike Markov chain based models, they can pass the hidden state to future time steps and update it as needed.

Thus, RNNs have desirable properties that may increase potential model performance compared to other approaches. RNNs have the ability to model long-range time dependencies as the hidden state can store information gleaned from any time period before, instead of being limited to the previous time step. They also have the ability to express a larger state-space than Markov chain based models. RNNs have been very successful in the fields of speech recognition and natural language processing. While not as pervasive as Markov chain based models in medicine, they have been successfully used to predict heart failure onset and clinical event occurrence.

RNNs can become difficult to train due to problems with error signal propagation, and this problem is exacerbated by the length of time span between signals. Though this is not a problem for every application of standard RNNs, there exist several modifications of standard RNNs to help overcome these issues: Long Short-Term Memory (LSTM) and Gated Recurrent Units (GRU). Both of these include modifications in the way the hidden state is computed, allowing models to explicitly forget previous information and input new information. GRUs share this modification; however, the forget and input operations are combined reducing the number of parameters in the model, potentially easing training.

2.2.3.3 Related Deep Learning Techniques

Deep learning allows models to learn feature representations as a part of model training. A special technique, called word embeddings, allow models to avoid the curse of dimensionality when handling high dimensional categorical values.

Categorical values are often embedded in a fixed size vector, where the components are binary. One hot encoding is a particularly popular approach as it ensures the present category is treated as independent to all the others. Unfortunately, these approaches scale linearly with the category dimension and also do not allow for encoding of relationships between categories. Word embeddings map category values to real-valued vectors, which can be updated over the course of training. After training, similar categories will have embedding vectors similar to one another. Once learned, embeddings can be reused and analyzed for representational meaning. They may also be used with graphical models that have distributed representations in the form of multiple latent variables.

Regularization is often employed for neural networks models, as their large number of parameters lead to a tendency to overfit. There are many strategies to prevent overfitting. The general ML techniques of L1 and L2 penalties hold for neural networks. They may be incorporated into the loss function to enforce a regularization objective, however this complicates the loss function. For clarity of initial understanding, some embodiments described herein have foregone penalties and instead employed another technique called early stopping. Early stopping involves monitoring the loss of the model on both training and out-of-sample data. Once out-of-sample loss starts to increase, the training is stopped. This technique is easily understood and implemented, allowing to easily use it as a part of our training and hyperparameter selection process.

2.3 Further Contributions of the Systems and Methods Described Herein

There is a need for new prediction methods that can be used to dynamically assess the likelihood of RTW. The following disclosure proposes a deep learning based model that yields daily predictions for the future work-status of patients given new information regarding treatment and recovery. Payers and clinicians may use embodiments disclosed herein to estimate future RTW outcomes, which may guide planning and decision making for populations of patients impacted by OIs.

3. METHODS

This section describes the methodological approach of certain embodiments described herein to create a dynamic prediction model for OIs. It is composed of the following subsections: 3.1) formulation, discussing the basic mathematical formulation of some embodiments; 3.2) data pre-processing, which covers how input data needs to be transformed for usage with some formulations; and 3.3) sequence to sequence learning, which covers some of the details regarding the training of certain RNNs.

3.1 Formulation

Some embodiments begin by providing a motivating example to help lay the groundwork for the model formulation. When a patient first experiences an OI, there is very limited data that may include the time and type of injury and basic demographic information about the patient. As time progresses, additional observations are acquired including diagnoses and treatments. These observations contribute to defining the patient's health status and may help predict the patient's future work-status. Over the course of an injured patient's case, from the first claim to the last claim, a patient's work-status may transition between not-working and working multiple times. Some embodiments aim to estimate the probability that they will be at work at a given future date (e.g. 30 days). Therefore, some embodiments treat RTW-status as a binary state variable that is perfectly observable.

In some embodiments, the formulation represents this dynamic information as two related sequences for each patient n: input observations up to and including period t, denoted by $X_{n,t}$ and the sequence of binary health-state variables representing RTW-status, $Y_{n,t}$. The entirety of both sequences for a given patient is referred to as that patient's trajectory. The input observations observed up to and including time t are referred to as the patient's history, $H_{n,t}$. Some embodiments seek to develop a model that learns the relationship between $X_{n,t}$ and $Y_{n,t}$, using all applicable information from $H_{n,t}$.

FIG. 1 illustrates an exemplary timeline 100 demonstrating the trajectory of a simulated patient. Outlined cells show the information contained for the input observation, history, and health-state variables at time 5, $X_{1,5}$, $H_{1,5}$, $Y_{1,5}$, respectively.

Generally speaking, $X_{n,t}$ may be very high dimensionality, because it includes diagnoses, treatments, and medications, each of which may have tens of thousands of unique values. In some embodiments, $X_{n,t}$ further includes vitals signs, laboratory tests, medical signs & symptoms, physician notes, biomarkers, and/or psycho-social information. This dimensionality is compounded when observations are recorded across time, which is the case for $H_{n,t}$. Thus, in order to train a model to learn the relationship between observations and health-states, it is not possible to directly utilize $X_{n,t}$ and $H_{n,t}$ to return $Y_{n,t}$. Instead, some embodiments may utilize a transformation that yields lower dimensional vectors $\tilde{X}_{n,t}$, $\tilde{H}_{n,t}$, and $\tilde{Y}_{n,t}$ respectively. In one example, the lower dimensional vectors have ten dimensions. The predicted values of $\tilde{Y}_{n,t}$ are $\hat{Y}_{n,t}$.

For each time-step, t, in a patient's trajectory, the model, f(·) takes an observation $\tilde{X}_{n,t}$ and the history up until this time-step $\tilde{H}_{n,t-1}$ to generate a new prediction $P_{n,t}$ and update the representation of the patient's history $\tilde{H}_{n,t}$.

$$P_{n,t}=f(\tilde{X}_{n,t},\tilde{H}_{n,t-1})$$

The training procedure described below results in $P_{n,t}$ between 0 and 1, that can be interpreted as probabilities. Some embodiments use these $P_{n,t}$ measures directly and also map them to 0 and 1 for categorization, which yields $\hat{Y}_{n,t}$.

3.1.1 Notation

To describe the details of the training procedure of some embodiments, the following will start by defining notation for indices, parameters, and features.

3.1.1.1 Indices and Parameters

To describe the details of some of the disclosed approaches, some notation will be defined as follows. Let $n \in \{0, 1, \ldots, N-1\}$ be the patient index, where N is the total number of patients. Let $t \in \{0, 1, \ldots, T-1\}$ be the time index, where T is the maximum relative time-units from a patient injury. Let $\varphi \in \phi$, where $\varphi$ is a specific feature index and $\phi$ is the set of all the feature names, defined by the dataset used. Let $\psi \in \psi$ where $\psi$ is a user defined offset, which is the forward prediction interval, and $\psi$ is the vector of all forward prediction intervals, note $\psi \subseteq \{0, \ldots, T\}$.

Note, n, t, φ are all defined by the given data and LP is user-defined.

3.1.1.2 Functions

TYPE(φ): is a function that returns the feature type of feature φ, which is a value in {Real, Low Dim Category, High Dim Category}. This function is user-defined for each of the features, it is recommended that features that contain real-valued data should be specified to the Real type, categorical data should be specified as either Low Dimension (Dim) Category (LDC) or High Dim Category (HDC).

Note that each categorical feature value is treated as belonging to a discrete set with a finite number of elements, that is defined by the given data, and denoted as $S_φ$. The TYPE function is user defined, but this disclosure recommends that categorical features with a small number of unique elements (<20) be specified as a Low Dim Category and that all remaining categorical features be specified as a High Dim Category.

OBSERVATION_TYPE(φ) is a function that returns the observation type of feature φ, which is a value in {Sample, Characteristic}. This function is also user-defined for each feature, and represents the temporal updating of this feature. Features with the observation type of Sample are expected to be dynamic data, representing observations over time. Characteristic features are expected to be static data, where the data is known at the beginning of time for a patient and is consistent across all time-steps.

3.1.1.3 Data Variables

Let $X_{n,t,φ}$ be the observation data for patient n, at time t, for feature φ. Note the relationship between the type of data contained in $X_{n,t,φ}$ and TYPE(φ), if TYPE(φ)=Real then $X_{n,t,φ} \in R$, if TYPE(φ)∈{LDC HDC} then $X_{n,t,φ} \in S_φ$. Some embodiments may suppress the individual features of the observation data for patient n, at time t, using a dot in place of the feature subscript, in the following manner: $X_{n,t,\cdot}$.

Characteristic observation type features do not have time dependency and thus for such a feature $φ_c$, the following relationship may be observed: $X_{n,0,φ_c} = X_{n,1,φ_c} = \ldots = X_{n,T-1,φ_c}$ and can suppress their time indices in the following manner: $X_{n,\cdot,φ_c}$.

The feature history is defined as $H_{n,t,φ} = X_{n,0 \ldots t,φ}$ where the history for patient n, at time t, for feature φ is the concatenation of all feature φ observation data for patient n, for all time-steps until and including t. Some embodiments let a patient's entire history be defined by $H_{n,t}$ which represents all observations for patient n, up to and including time t, for all features in φ.

Some embodiments let $Y_{n,t}$ be the future outcome vector for patient n at time t+ψ. $Y_{n,t}$ is a binary vector of dim(ψ), as there will be one predicted outcome for each of the offset intervals in ψ. Each of these data variables $X_{n,t}$, $H_{n,t}$, $Y_{n,t}$ will be transformed by the approaches described herein and these transformations are labeled $\tilde{X}_{n,t}$, $\tilde{H}_{n,t}$, and $\tilde{Y}_{n,t}$ respectively.

TABLE 2

Formulation overview accompanied by example data. Data represents time period 1 for patient 1 (depicted pictorially in FIG. 1).

| | Formulation | Example Data |
|---|---|---|
| Parameters | N: number of patients<br>T: maximum relative time since injury<br>φ: the set of features (provided by user)<br><br>Ψ: offset - forward prediction interval(s) | N = 100<br>T = 10<br><br>φ = {Age, Sex, Job, Diagnoses, Treatments and Tests, Medications, Health Status}<br>Ψ = [1] |

TABLE 2-continued

Formulation overview accompanied by example data. Data represents time period 1 for patient 1 (depicted pictorially in FIG. 1).

| | Formulation | Example Data |
|---|---|---|
| Index Variables | n ∈ {0, 1, . . . , N − 1}: patient index<br>t ∈ {0, 1, . . . , T − 1}: time index<br>φ ∈ Φ: feature index<br>ψ ∈ Ψ: offset index | n ∈ {0, 1, . . . , 99}<br>t ∈ {0, 1, . . . , 9}<br>φ ∈ Φ,<br>ψ = 1 |
| Functions | TYPE(φ) ∈ {Real, LDC, HDC} determines feature type | TYPE (Age) = Real<br>TYPE(Sex) = LDC<br>TYPE(Job) = HDC<br>TYPE(Diagnoses) = HDC<br>TYPE(Treatments&Tests) = HDC<br>TYPE(Medications) = HDC<br>TYPE(Health Status) = LDC |
| Data Variables | $X_{n,t,φ}$: Samples - an observation value for patient n, at time t, for feature φ.<br>$H_{n,t,φ}$: feature history - represents the history of values for patient n, up to and including time t, for feature φ.<br>$Y_{n,t}$: future outcome (work-state) for patient n at time at t + φ | $X_{1,1,Diagnoses}$ = "Lower Back Sprain"<br><br>$H_{1,1,Diagnoses}$ = [∅, "Lower Back Sprain"]<br><br>$Y_{1,1,Diagnoses}$ = Not Working = 0 |

3.2 Data Pre-Processing & Transformation

In some embodiments, the feature preparation and transformation pipeline consists of several major steps: filtration, aggregation, and normalization. All together, these steps ensure that patients missing vital data are not used for training or evaluation, that each time-step observation is consistent, and that the data presented to the models is optimized for training.

3.2.1 Filtration

Patients missing data from necessary features are removed in the filtration step. Necessary features are a subset of the features that each patient must have in order to be included in the study. Generally, this disclosure recommends that characteristic features be the only type of feature included in the necessary feature set, as the absence of a sample feature is treated as informative. After patients with missing data are filtered out of the dataset, the dataset is split into independent datasets for training, development, and testing.

3.2.2 Aggregation

The aggregation step ensures that all patient observation samples contain information for equivalent time intervals. An observation time interval is selected and then all samples for every patient are mapped into a new relative time space ($\tilde{T}$) that represented the number of time intervals from the index time (date of patient injury) which is indexed by $\tilde{t}$. Aggregation functions are run over this $\tilde{T}$ for each patient and feature. These functions help to build a representation of each feature that is consistent across time-steps.

Different aggregation functions are designed for each feature type. Real feature types have natural mathematical aggregations, such as mean, standard deviation, min, max, count, etc. Each of these functions are evaluated for all the sample values that map to a given $\tilde{t}$, for each patient and feature.

Low Dim Categories and High Dim Categories are slightly more complicated, due to the fact that they often represent abstract concepts and do not have natural aggregation functions. The aggregation of both categorical types is optimized for their representation to the RNN. Low Dim Categories are represented with aggregates of one-hot-encodings. One-hot-encodings can efficiently represent categorical values with low dimensionality and are relatively interpretable for lay users. All categorical sample values for each Low Dim Category feature are converted to one-hot-encoding vectors, each of the values in one-hot-encoding vector values are then aggregated at every $\tilde{t}$. Since these values are real values (either 0 or 1), some embodiments are able to use mathematical aggregation functions, namely the mean function High Dim Categories represent a larger space of information and are ill-suited for one-hot-encoding. Some embodiments seek representations of High Dim Category that are both space efficient and can capture clinical meaning, as such, some embodiments employ the concept of word-embeddings. Every High Dim Category value is mapped to an embedding, a real-space vector with dimension proportional to the number of distinct category values. Embeddings are randomly initialized and are updated during training. Untrained embeddings can be only directly aggregated via mathematical functions if aggregation is carried out as part of the learned model.

Some embodiments handle aggregation by fixing the number of sample observations per $\tilde{t}$, this number is called the channel size (C), yielding a fixed length vector. If the number of High Dim Category feature sample observations in a given patient's $\tilde{t}$ is larger than C, those sample observations are randomly resampled to yield C observations. A special "no-category value observed" token is used to fill channel positions that are left unfilled due to observing less than C samples in a time-step $\tilde{t}$.

The aim of the aggregation step is to yield a consistent representation across every time-step for each patient's features. Some patient feature time-steps may not contain any aggregated data, this is handled in the normalization step, which also promotes effective model training.

3.2.3 Normalization

In addition to handling time-steps without aggregate data, normalization has two primary purposes: 1) censoring very rare data; and 2) rescaling feature data ranges for effective training. Time-steps without aggregate data are handled during the rescaling process. Like aggregation, these procedures for normalization of a feature depend on the type of the feature.

3.2.3.1 Rare Values

Very rare values can be problematic for both training and inference. Very rare values in training sets present the opportunity for models to over-fit and trained models cannot handle previously unseen rare category values at inference time. In order to prevent these issues some embodiments use simple filtration and replacement methods for each of the different feature types.

Extreme outliers are the primary very rare data values of concern for Real feature types. These values are easily handled by restricting the range of each feature type to the mean±3 standard deviations. Any values greater (or smaller) than that range are converted to the maximum (or minimum) range value.

For efficiency, Low Dim Category features have their rare data removed as part of the aggregation process. At the time of aggregation each of the unique values for a Low Dim Category are counted and all unique values with a count less than 10 are replaced with a special "other category value" token. Aggregation then proceeds in the manner described above.

Unlike Low Dim Categories, High Dim Categories must be aggregated first as re-sampling will affect the unique value counts. After aggregation the count occurs, unique values with a count less than 10 are replaced with special "other category value" token. After rare data has been handled, each feature is then re-scaled.

3.2.3.2 Re-Scaling

For each patient feature time-step, one of two things is done: if data exists for that time-step it is rescaled, if there is no data in that time-step default place-holder values are determined and inserted at training time by the data generation function.

Real feature types have existing data rescaled to a standard normal space (standardized) by subtracting the mean and dividing by the standard deviation of the feature value across all patients and all $\tilde{t}$. If data is does not exist for a time-step it is filled with zeros, which is equivalent to mean-imputation.

Low Dim Category features are not rescaled, as their range should naturally fall between 0 and 1, which is acceptable for neural network training. Non-existent time-step data are filled with zeros, as this is a natural representation of the proportion of a non-observed category value. NOTE: Low Dim Categories could be treated equivalently to Real features as they also take the form of real-values after aggregation. This is unnecessary because the acceptable natural range of the mean aggregation and an additional rescaling adds complexity.

High Dim Categories do not need to be rescaled as their corresponding embedding vector values are initialized to an acceptable range. Non-existent time-step data is filled with a vector of "no-category value observed" tokens.

Normalization helps to handle time-steps without aggregated data, censors very rare data, and promoted effective training. After this step, some embodiments have completed the transformation of the raw input data $X_{n,t}$ to $\tilde{X}_{n,\tilde{t}}$.

3.2.4 Health-State Variable

The health-state (outcome) variable $Y_{n,t}$ is generated from each patient based on a list of dates. In some embodiments, the claims dataset includes lists of leave and return to work dates for each patient. For each time-step between a patient's leave and return date pair, the health-state variable ($Y_{n,t}$) is set to 1, otherwise it is set to 0. $Y_{n,t}=1$ represents a time-step t where patient is at work and $Y_{n,t}=0$ represents a time-step where the patient is away from work. Thus, patients that leave work multiple times have a health-state sequence with alternating periods of 1s and 0s. If a patient is injured and never leaves work their health-state sequence will be a series of 1s, and for patients that leaves work and never returns their health-state sequence is a series of 0s.

Since it is useful to predict a future health-state, some embodiments re-index the time-steps of the outcome variable. This re-indexing is done via an operation known as left-shifting which uses $Y_{n,t}$ and the $\psi$ parameter, which may be a scalar or a vector. For each component of $\psi \in \psi$, a new $\tilde{Y}_{n,t,\psi}$ component is created that contains the value $\tilde{Y}_{n,t-\psi}$. Time-steps that left-shift beyond the last time-step simply replicate the value of the last time-step.

3.3 Sequence to Sequence Learning

Some embodiments use an RNN to build a model that maps the input sequences ($\tilde{X}_{n,t}$) to the output sequences ($\tilde{Y}_{n,t}$), while simultaneously building and utilizing history representations ($\tilde{H}_{n,t}$). Some embodiments use the above transformation methods to pre-process the data. To train the model, some embodiments use an objective function that minimizes binary-cross entropy and/or use a special generator function to pad the variable lengths of patient sequences in a set batch.

3.3.1 Architecture

There are three major components of the models that some embodiments use for this sequence-to-sequence learning task. The first is a series of layers to ingest input data at each time-step $\tilde{X}_{n,t}$, the second uses RNN layers to build a history representation, and the last transforms the history representation into a prediction for the time-step.

$$\tilde{\tilde{X}}_{n,t} = f_{ingestion}(\tilde{X}_{n,t})$$

$$\tilde{H}_{n,t} = f_{middle}(\tilde{\tilde{X}}_{n,t}, \tilde{H}_{n,t-1})$$

$$P_{n,t} = f_{final}(\tilde{H}_{n,t})$$

Ingestion layers are automatically constructed by the fitted pipeline defined above. Due to the special representation of the different types of features, there are several types of input layers which are designed to receive the various features of each $\tilde{X}_{n,t}$ vector. Ingestion layers embed High Dim Category features from an input vector, $\tilde{X}_{n,t}$, and subsequently concatenate those values to the remaining $\tilde{X}_{n,t}$ vector values, creating a representation ideal for the following RNN layers to utilize ($\tilde{\tilde{X}}_{n,t}$).

Although various configurations may be used for the middle component, they will all have some variation of an RNN, which will allow a $\tilde{H}_{n,t}$ representation to be built. These $\tilde{H}_{n,t}$ representations are then passed to the final component which produces a prediction $P_{n,t}$. There may be a series of dense layers used; however, the final layer must yield values between 0 and 1. This is achieved through the use of a sigmoid activation function. The real-valued values passed into the sigmoid function can be thought of log odds, which when passed through a sigmoid function yields probabilities. Because of their flexible design, both the middle and final component are subject to extensive hyperparameter exploration, which is discussed later.

3.3.2 Loss Function

Because some embodiments seek to predict the value of binary variable ($\tilde{Y}_{n,t}$), some embodiments use a maximum likelihood approach to define a Bernoulli distribution that is conditioned on the sequence of inputs $\tilde{X}_{n,t}$. This approach requires that predictions be generated by a sigmoid function, as mentioned above, and that binary cross-entropy loss be minimized.

Cross-entropy can be used as a distance metric between two distributions sharing the same set of states. Identical distributions produce a cross-entropy of 0 and higher values indicate a difference between the distributions. The difference between two distributions is often measured by the KL divergence; minimizing this is equivalent to minimizing the negative log-likelihood and the binary-cross entropy between observed $\tilde{Y}_{n,t}$ and predicted $\tilde{\tilde{Y}}_{n,t}$, which is $P_{n,t}$ rounded.

This loss function may be modified with regularization techniques, L1 or L2 regularization, ensembles, or multi-task learning. Some embodiments have focused only on the usage of early-stopping during training, due to its ease of implementation and understandability.

3.3.3 Variable Sequence Length

While RNNs can theoretically handle sequences of any length, there are performance issues that arise when using variable length sequences during training. Typical training procedures expect sequences of equal lengths in each training batch. In some embodiments, sequences are of variable length, since they contain all the time-steps between a patient's first claim and their last claim. At training time, in some embodiments, these sequence lengths are standardized with two techniques: first, extremely long sequences are truncated; second (and subsequently), the length of short sequences are padded.

Some embodiments truncate patient sequences that are extremely long, using a parameter L, all observations where t>L are ignored. Despite employing truncation, some embodiments still have variable length sequences at training time. Employing truncation alone is problematic, as it restricts learning relationships beyond the length of the training sequences, and does not resolve length issues for sequences that are shorter than the truncation length. Most sequences are not truncated and are instead padded dynamically at training time. Padding aims to lengthen all sequences to the maximum sequence size, thus helping to avoid this issue of shorter sequences. However, padding creates two sub-issues that must be resolved for effective training.

Globally padding all sequences to the same length is inefficient in terms of memory usage as all sequences are now forced to be as long as the longest sequence, which can be arbitrarily long. Some embodiments resolve this by creating a data generation function that pads data in batches, as each batch is being fed to the training procedure. This allows to store the sequences as their normal length form and conduct lengthening dynamically. During training, batches of inputs ($\tilde{X}_{n,t}$) are selected and then each patient sequence is lengthened to the length of to the longest sequence in the batch.

The second issue is that of error assignment. Because loss errors are calculated for every timestep output, the padded time-steps could contribute to the training loss. This is not desirable, as the padded values have no relationship to the task some embodiments seek to achieve. To avoid this, some embodiments implement a masking function that prevents the padded time-steps from contributing to the loss. Together, padding and masking allow to efficiently train on sequences with variable lengths.

4. OCCUPATIONAL INJURY CASE STUDY

In accordance with the systems and methods described herein, an experimental case study was conducted using a large set of retrospective patient injury data, which was used to select, train, and evaluate a model. The following sections address the data, how the models were evaluated, various architectural choices, training procedures, and experimental results.

4.1 Data

A dataset was used that contains 1.2 million patient injuries, all from a single midwestern state, that occurred from 2000-2010. The dataset has two main components, demographic information and observational data. Demographic data (e.g. age, sex, job) is static characteristic information that is known at the time of injury. Observation sample data (e.g. diagnoses, procedures, RTW dates) are all accompanied by a date, and are presumed to be observed on this date. Institutional Review Board (IRB) approval was obtained to conduct research on the Peers Health dataset, which was used as an example to establish a proof of concept for the approaches described herein. In some embodiments, a data transformation pipeline was implemented using python, and example code is included in FIGS. 6A and 6B (FIG. 6B is a continuation of the example code of FIG. 6A).

Of the 1.2 million patient injuries available in the Peers data set the experiment, and all patients were included.

Data was split into training, validation, and testing datasets (80/10/10%). The pipeline parameters were $\psi=1$, C=5, L=500, and a daily time-granularity. The training set was used to fit functions for the filtration and normalization steps, minimizing information leakage and allowing for transformations to be replicated across dataset partitions. The pipeline was then used to transform each of the datasets, yielding $\tilde{X}_{n,t}$ and $\tilde{Y}_{n,t}$ for each patient-day.

Note, the $\tilde{X}_{n,t}$ and $\tilde{Y}_{n,t}$ sequences are of variable length, with each patient's sequence length being dependent on their claim duration (time from first claim to last claim). However, at each time-step the dimensionality of information is consistent, due to the steps described above.

4.2 Evaluation

In line with the approach outlined above, some embodiments aim to use the transformed data to build a daily prediction of future work-state. Collectively, these dynamic predications will be assessed in terms of both discriminative performance and calibration. Through the learning process the $\tilde{P}_{n,t}$ is naturally bounded between 0 and 1, and can be interpreted as probabilities of being at work.

These probability values can be assessed for calibration and be used to generate discriminative categories, not working vs working. The discrimination is the primary measure and is assessed by the area under the receiver operator characteristics curve (AUROC). Personalized predictions can also be recovered from the model and are assessed graphically against the actual work trajectory of a patient.

4.3 Neural Network Architectures

In some embodiments, the pipeline automatically generates portions of the neural network so the transformed data, $\tilde{X}_{n,t}$ and $\tilde{Y}_{n,t}$, can easily be deployed against a user's preferred architecture.

The entire ingestion layer is constructed by the pipeline according to the specifications of the given data. These components help to convert $\tilde{X}_{n,t}$ to $\hat{X}_{n,t}$ and are detailed in the table below. The HDCs were converted to embedding categories and channelized (C=5) by the pipeline. Embedding sizes were sized proportional to the recommended quarter-power rule of thumb $\sqrt[4]{\text{Dim(HighDim.Category)}}$.

TABLE 3

Data tables and columns available from Peers dataset.

| Table | Column | TYPE | Network Ingestion Components |
|---|---|---|---|
| Demographics OT: Characteristics | Age | Real | Age_norm |
| | Gender | LDC | Gender_{F, M, NaN, Other} |
| | NCCI-Code | HDC | NCCI-Code_embd |
| Diagnoses OT: Samples | ICD9-Code | HDC | ICD9-Code_embd_c_0 . . . ICD9-Code_embd_c_4 |
| Procedures OT: Samples | Procedure-Code | HDC | Procedure-Code_embd_c_0 . . . Procedure-Code_embd_c_1 |
| | Units | Real | Units_min Units_average Units_max |
| | Diagnosis | HDC | Diagnosis_embd_c_0 . . . Diagnosis_embd_c_1 |
| Other-Procedures OT: Samples | Procedure-Code | HDC | Procedure-Code_embd_c_0 . . . Procedure-Code_embd_c_1 |
| | Diagnosis | HDC | Diagnosis_embd_c_0 . . . Diagnosis_embd_c_1 |
| Work-status OT: Samples | Working | Real | Working |

In Table 3, feature configuration in terms of feature TYPE is described at the column level and in terms of OBSERVATION_TYPE (OT). OT is described at the table level. The final column shows the names of the transformed features and their corresponding ingestion layers in the automatically created ingestion layer of the neural network architecture.

The middle component has the most possible potential for variation. Some embodiments were used to test different RNN implementations, including Simple RNNs, LSTMs, and GRUs; other variations may also be employed in this component. Some of the architectures ranging from very deep networks (>5 RNN layers), to wide networks (width measured by the dim($H_{n,t}$), wide being >64) with a majority of architectures exploring a medium between those extremes (e.g. 3 deep and 32 wide).

Some architecture exploration was conducted with the final component as well, with the number of dense layers and their widths being varied. All configurations had a final dense layer with a sigmoid activation function and the same output size as the size of $\psi$.

Figure 2:
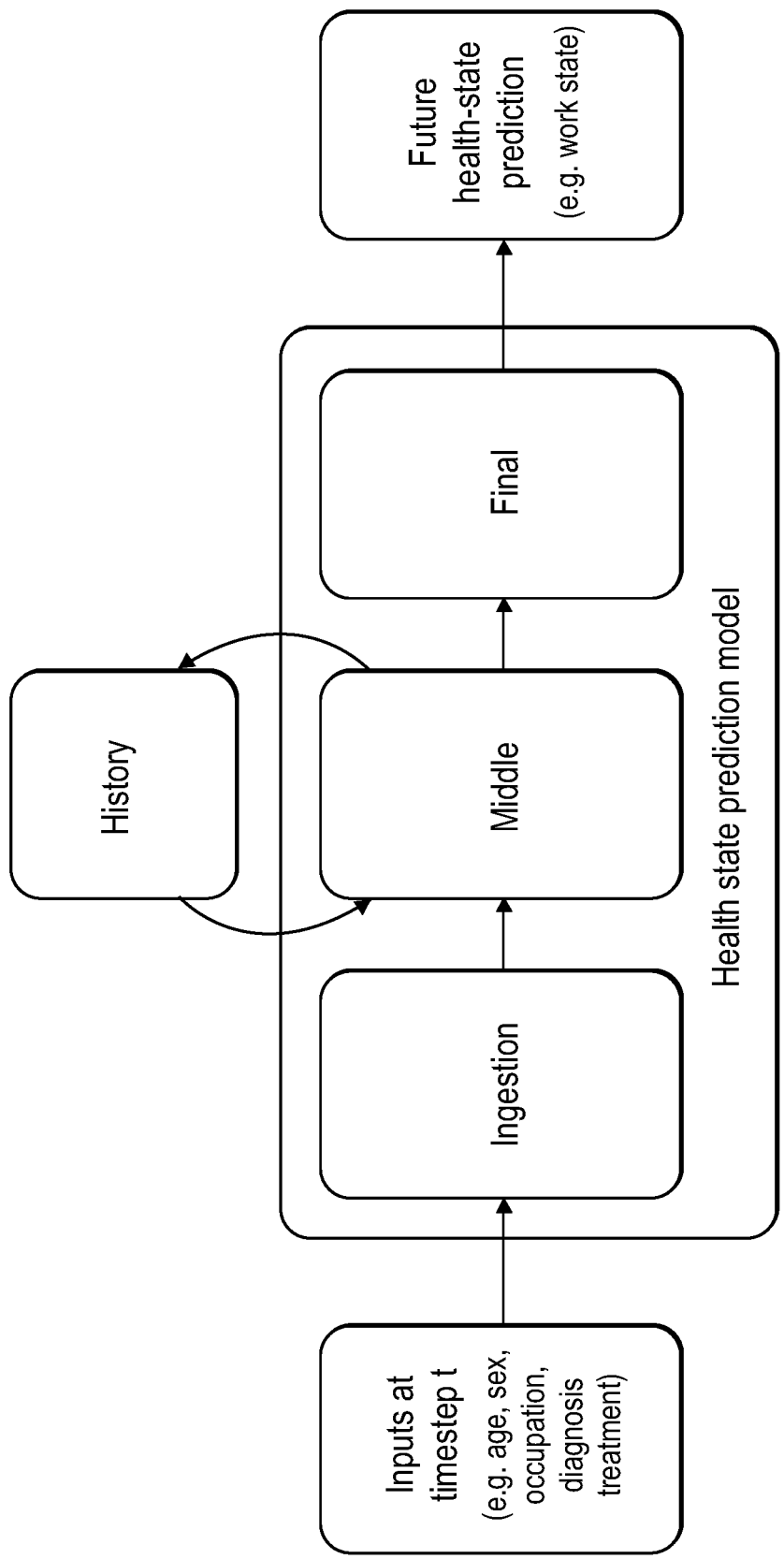
FIG. 2 shows a schematic representation of the general architecture of an embodiment of the dynamic prediction model.

FIG. 2 shows a schematic representation of the general architecture of an embodiment of the dynamic prediction model. Inputs are ingested, and passed through their respective embedding layers, if necessary. They are then concatenated and passed to the middle component, and finally fed to the final component which returns a prediction for the future RTW status.

TABLE 4

Feature Embedding in accordance with systems and methods disclosed herein.

| Table | Feature | Number of Categories | Recommended Embedding Size | Embedding Table Parameters |
|---|---|---|---|---|
| Demographic | NCCI Code | 631 | 5.0 | 2570 |
| Diagnosis | ICD 9 Code | 3,565 | 7.7 | 7602 |
| Procedure | Procedure Code | 20,264 | 11.9 | 54117 |

4.4 Training Procedure & Hyperparameter Search

Models were trained on a workstation running Ubuntu 18.04.2, with 256 GB memory, 24 CPU cores and a Titan V graphics card (12 GB memory). TensorFlow 2.0 was run using a Docker and Nvidia Docker instances.

Data was processed by a pipeline which returned a python data generator function for training. Various model architectures were trained with the training data, with out-of-sample performance measured on the development dataset. Training was conducted using the ADAM optimizer. Each model was allowed to run for 20 epochs (full iterations over the training data set), with batch sizes of 64, results were stored every epoch, and TensorBoard was used to evaluate training. Model training time ranged from 20 minutes per epoch to 2 hours per epoch, in relation to the number of parameters used.

Most architectures yielded similar performance in terms of the primary loss function, binary cross entropy, and secondary measures such as accuracy and mean squared error. Some embodiments chose to use a final architecture comprising or consisting of the standard ingestion components, with a middle component of an LSTM layer with dim($H_{n,t}$)=32, followed by a final component consisting of two layers, the first a 32 wide and the second 1 wide with a sigmoid activation. This yielded a network with 73,186 parameters, and was run for 4 epochs based on the early stopping regularization approach.

4.5 Experimental Results

The selected model was trained on the training data for 4 epochs and then evaluated on out-of-sample development data. Some embodiments utilized the SKLearn package to calculate the model performance metrics, comparing the actual daily outcome values ($\tilde{Y}_{n,t}$) with predicted daily outcome values generated by the model $P_{n,t}$.

Model discrimination was tested by evaluating receiver operator characteristics (ROC) of the model's predictions against the known outcomes. All daily patient predictions and daily known outcome values for the development set were used to generate an ROC curve and calculate the area under it.

Figure 3A:
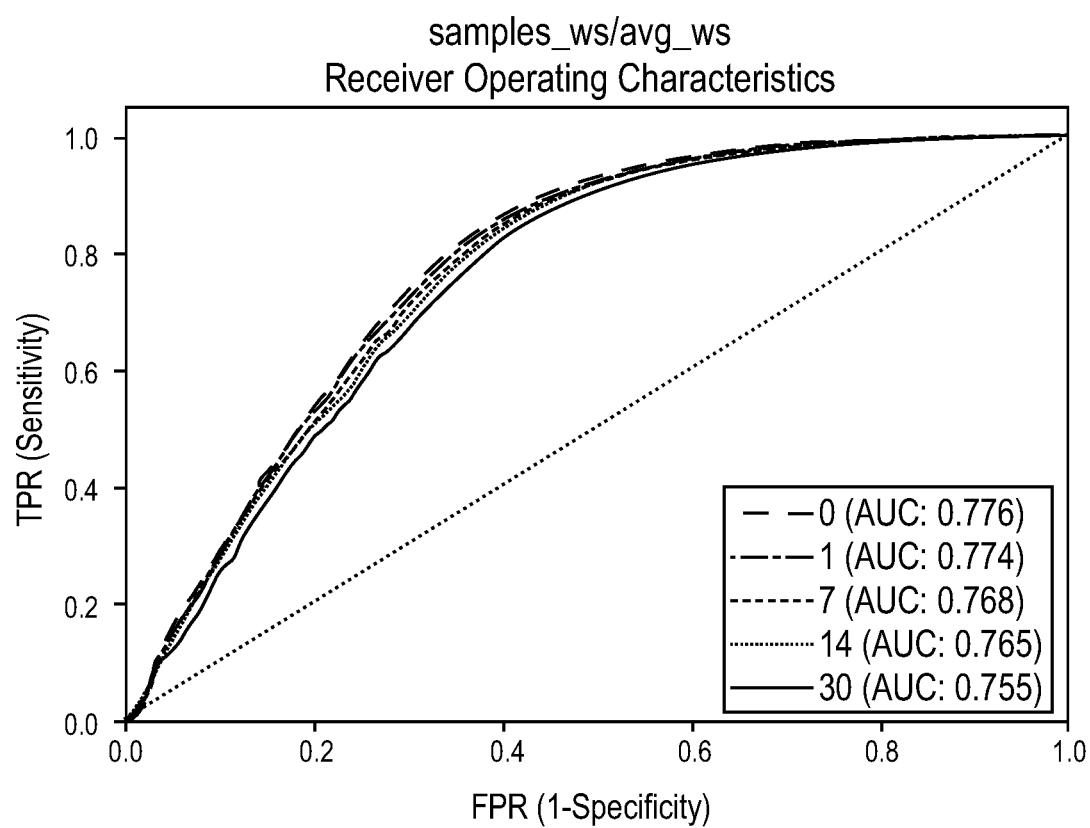
FIG. 3A shows discriminative performance of examples of learned models. It should be noted that performance may change depending on architecture and choice of inputs.

FIG. 3A shows discriminative performances of example learned models; as shown, the receiver operator characteristics curve demonstrated the discriminative performance on the out-of-sample development set (area under curve (AUC) results shown in FIG. 3A).

Figure 3B:
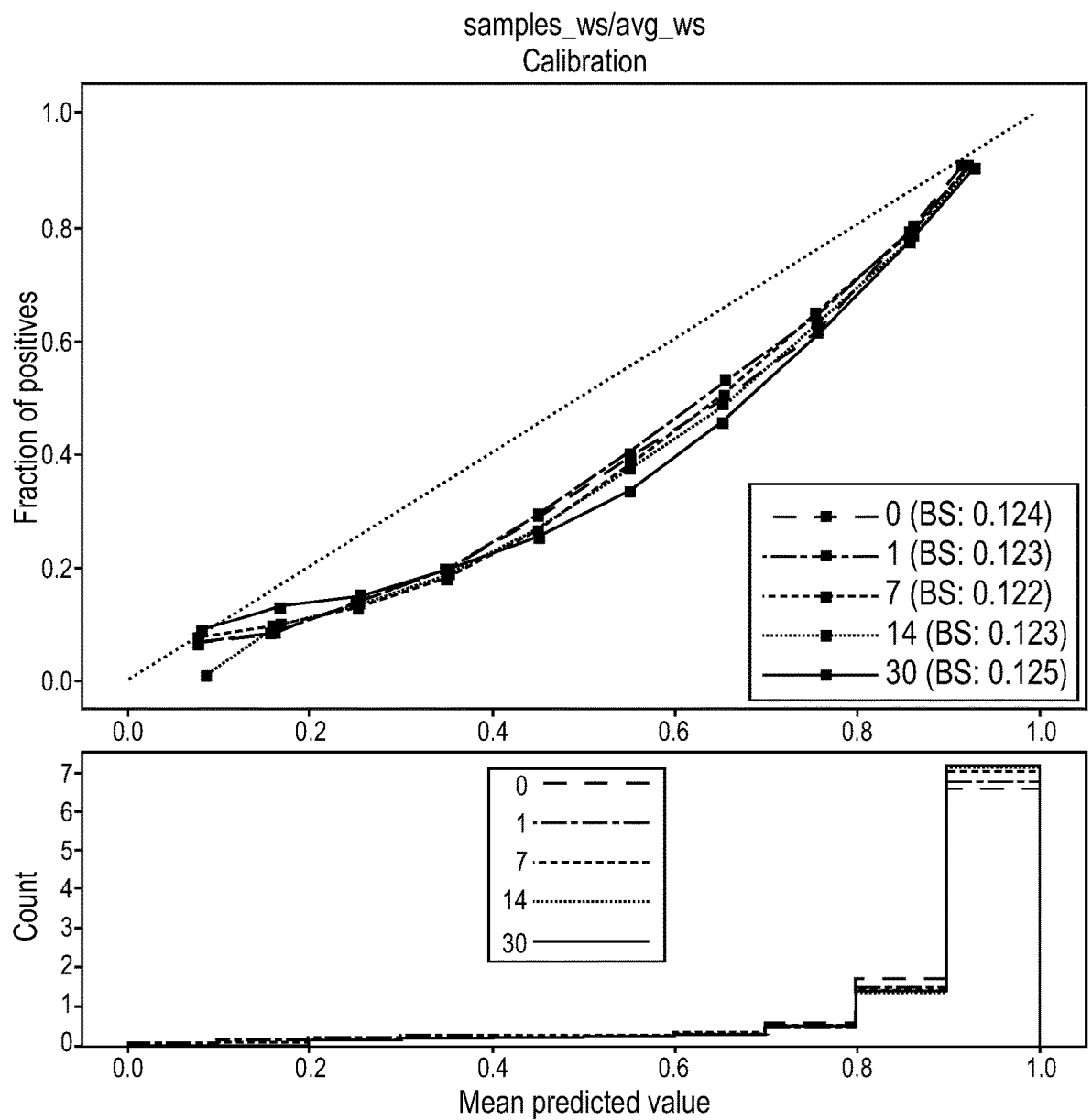
FIG. 3B shows calibration of an example learned model; as shown, the decile calibration curve demonstrates the calibration of the model probabilities against the actual future work status of each predicted patient day. It should be noted that performance may change depending on architecture and choice of inputs.

FIG. 3B shows calibration of the learned model; as shown, the decile calibration curve demonstrates the calibration of the model probabilities against the actual future work status of each predicted patient day.

Model calibration was tested in terms of the Brier score and by generating a calibration plot. Both used the same sets of data used for discrimination analysis, the daily patient predictions and actual values. The calibration plot was produced by binning all the daily predictions into deciles, then calculating the average predicted value and the fraction of actual positive for each decile. The slope of these plots match the ideal 1:1 line well.

Figure 4:
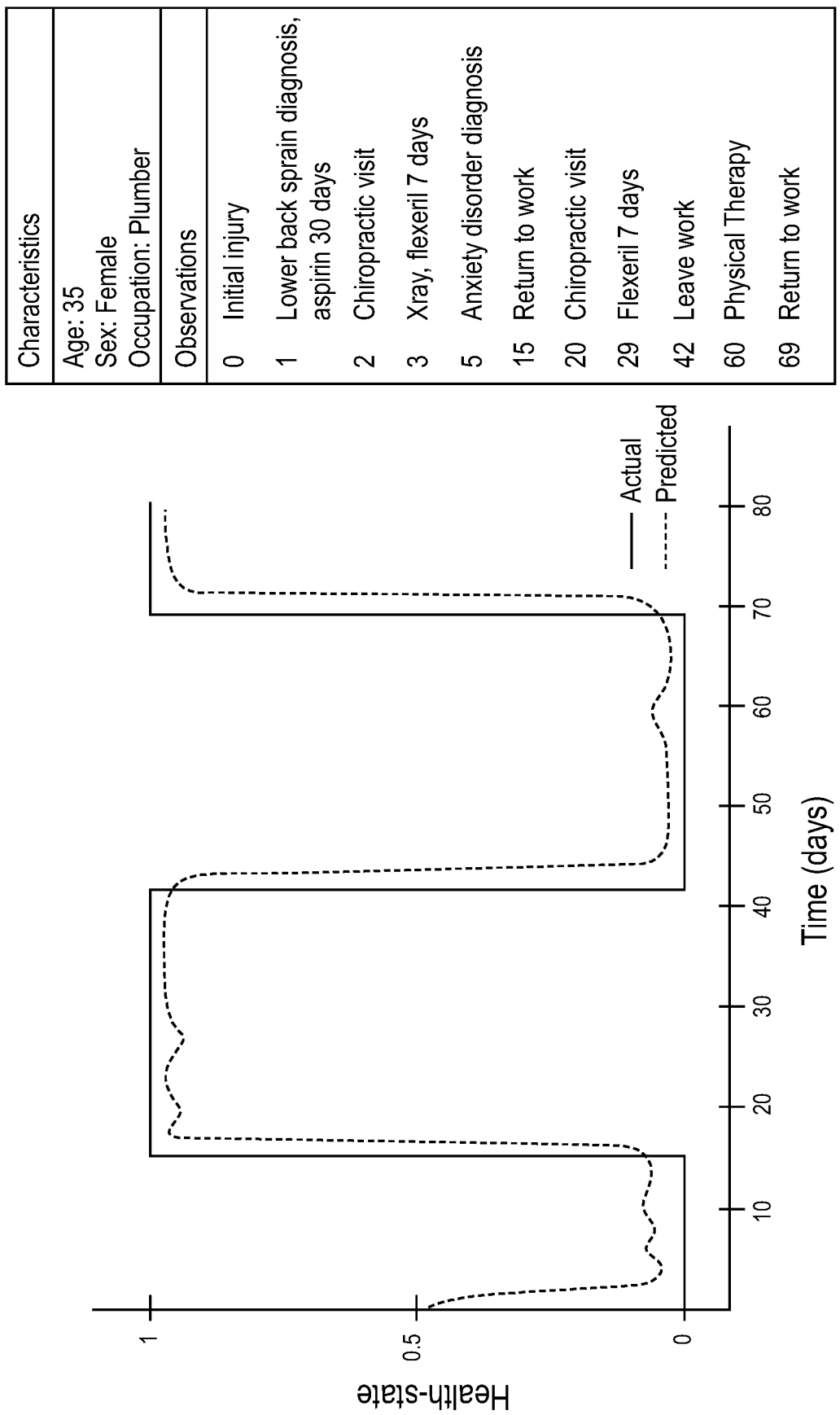
FIG. 4 illustrates predicted values and patient trajectory for a randomly selected patient from the out-of-sample development set.

Daily prediction scores can also be analyzed across the trajectory of historical patients. When plotted across time, they represent a curve that reflects the evolving knowledge of the injured patient. Daily predictions can be generated from the model by feeding the input sequence into the model. The outputted predictions can be plotted against the known RTW and leaving work events, and contextualized to gain insight into the model's prediction approach. In FIG. 4, an example patient's predictions are depicted over-time, along with descriptions of the patient's injury and their recovery trajectory.

FIG. 4 illustrates predicted values and patient trajectory for a randomly selected patient from the out-of-sample development set. The shown curve depicts the daily predictions of the model (dashed line) and when the patient actually returned to work (vertical solid date-line). On the right is a time-line of all the diagnostic and treatment events that occurred for this patient.

5. DISCUSSION

The foregoing has demonstrated the utility of the disclosed model for large-scale RTW prediction through an experimental case. Using the data transformation pipeline, the approaches disclosed herein transformed over 500 thousand patient injury claims records into injury trajectory sequences. Some embodiments used these patient injuries to train and test a recurrent neural network to predict future work status every day for each of these patients.

These results show promise for predicting RTW for injured patients, with example results shown in FIGS. 3A and 3B. When assessing individual level predictions, the approaches disclosed herein realized desirable characteristics, such as a rise in probability over 0.5 before an RTW event occurs and a relatively stable high probability while the patient remains working. It is believed that this represents a significant advance in the state of the art, as these are the first models to deliver accurate dynamic prediction.

Occupational injuries cause an immense burden and managing the recovery process of injured patients is very a difficult task. Models exist to predict the amount of time it will take an injured patient to return to work, however they are static and often use specially collected data. These characteristics have limited the utility of existing models, and prevent their widespread use in guiding resource allocation and influencing patient treatment decisions overtime. The approaches disclosed herein introduce a new deep learning based approach that utilizes administrative claims data to accurately dynamically predict the future RTW status of injured patients. In the disclosed approaches, each patient's trajectory is represented as two related sequences; the first is a series of observations of the patient's injury and treatment history, and the second is a sequence representing the health-state of the patient. Some embodiments are able to build a representation of the patient's history, which then is used to produce a prediction for the health-state of the patient at a given moment in the future. As time progresses and new treatments are rendered, the observation sequence is updated and a new prediction can be produced.

This sequence-to-sequence learning is enabled through the use of recurrent neural networks, a deep learning technique. High dimensionality in observed data presents a significant modeling challenge. Accurate high-fidelity representations of some observation features, such as diagnoses and treatments, would be intractable without deep learning techniques. By pairing embeddings with RNNs our model is able to efficiently represent observed information and patient histories.

5.1 Limitations

These results are promising for this first application of deep learning to predictive modeling for RTW. The disclosed study focuses on using administrative claims data that is collected by state workmen's compensation agencies. Many other RTW studies use specially collected data, which often measure important patient, work-place, and psycho-social features. These data are generally not present in administrative data, but their addition may improve performance if utilized in future embodiments of the approach.

One major consideration with the usage of deep learning techniques is that of interpretability. Due to their architecture and large number of parameters, RNNs are notoriously difficult to interpret, making some models a "black box." This would be an issue if users sought to use it to guide treatment decisions, as there are few effective ways to probe and validate the decision making of the model. It is possible that usage on a larger scale, such as by insurers, does not necessitate the same level of interpretability, as the intended usage is over populations of patients, not individual patients.

A final consideration is the external validity of the model. It was trained on a large cohort of patients injuries; however, they are all from the same state and time period. Thus, the model may be sensitive to large scale changes over time. One such change is the recent shift in opioid based analgesics prescription, which would not have been captured in the dataset. Potential performance characteristics should be carefully evaluated before usage in a new setting and once implemented model performance should be continuously monitored.

6. CONCLUSIONS

The above limitations notwithstanding, it is believed that the approaches disclosed herein lay the foundation for future studies. The disclosed initial results are promising, and indicate that the model should be trained and evaluated for usage as the immediate next steps.

The foregoing has shown that it is possible to use routinely collected and widely available data to predict RTW. This is the first such study to conduct large scale RTW prediction with administrative claims data. It is also believed that this is also the first study that uses deep learning to address the problem of predicting RTW. Deep learning allows this new approach to build a dynamic model of a patient's future work-state following an occupational injury. In aggregate, such estimates for panels of patients overseen by clinicians and insurance agencies can help direct limited resources to patients at greatest risk of protracted recovery.

EXAMPLE EMBODIMENT

Figure 5:
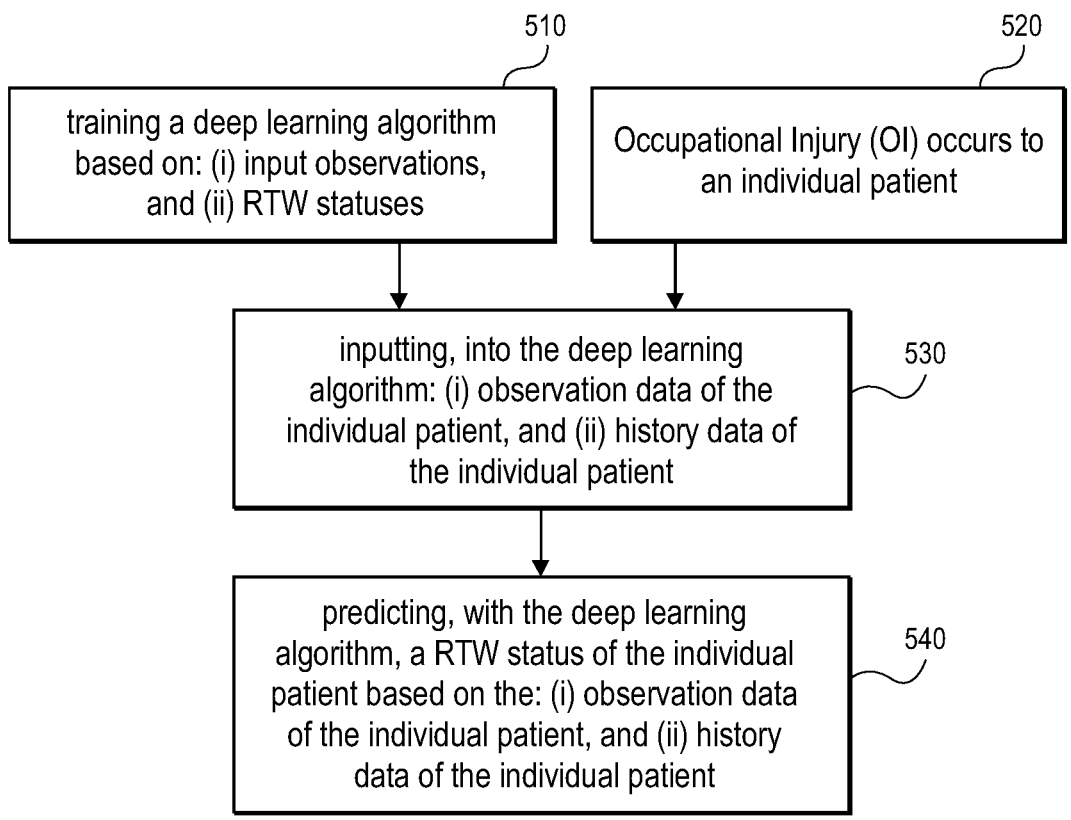
FIG. 5 illustrates a flowchart of an example embodiment.

FIG. 5 illustrates a flowchart of an example embodiment. With continuing reference thereto, at step 510, a deep learning algorithm is trained based on: (i) input observations ($X_{n,t}$) (which may include both static and dynamic data), and (ii) RTW statuses ($Y_{n,t}$). The training may include transforming matrixes of the input observations, patient histories, and RTW statuses into lower dimensional vectors. The training may further involve using an objective function to minimize binary-cross entropy between a vector of the input observations and a vector of the RTW statuses; and/or using a special generator function to pad variable lengths of the input observations.

At step 520, an OI occurs to an individual patient. At step 530, the deep learning algorithm receives inputs of: (i) observation data of the individual patient, and (ii) history data of the individual patient. At step 530, the deep learning algorithm is used to predict a RTW status of the individual patient based on the: (i) observation data of the individual patient, and (ii) history data of the individual patient.

ADDITIONAL EXAMPLE EMBODIMENT

Additionally or alternatively to predicting RTW or work status, the systems and methods described herein may be used to predict other health-states or medical conditions. For example, sepsis may be predicted; in this regard, a patient's sepsis status may be treated as the binary health-state variable. In another example, cancer may be predicted, and a patient's cancer status may be treated as the binary health-state variable. (In this regard, it should be understood that the proposed approaches can be adapted to categorical variables of higher dimension (not just binary) which would be important for things like cancer (there are multiple types in most cases) and blood pressure (a continuous measure that would be discretized—for example, low, medium, high)).

In another example, example of future values of systolic blood pressure may be predicted, and a patient's systolic blood pressure may be treated as a real valued or continuous health-state. In another example, diabetes may be predicted, and a patient's diabetes status, non-diabetic, pre-diabetic, and diabetic, may be predicted as a categorical health state. Moreover, it should be understood that all of the forgoing techniques may be applied to predicting sepsis, cancer, blood pressure states and other medical conditions. Furthermore, the above-described techniques may be applied outside of healthcare problems (e.g. predicting machine reliability, predicting financial status of a borrower, etc.). Indeed, the foregoing techniques can be adapted to predicting the probability of a "system" being in any of a discrete and finite number of "states."

Thus, in one aspect, there is a computer-implemented method for predicting a system being in a state, the method comprising, via one or more processors:

training a machine learning algorithm based on: (i) input observations, and (ii) states;

inputting, into the machine learning algorithm, observation data of the system; and predicting, with the machine learning algorithm, the system being in the state based on the observation data of the individual patient.

In another aspect, there is a computer-implemented method for predicting sepsis of an individual patient, the method comprising, via one or more processors:

training a deep learning algorithm based on: (i) input observations, (ii) patient histories, and (iii) sepsis statuses;

inputting, into the deep learning algorithm: (i) observation data of the individual patient, and (ii) history data of the individual patient; and predicting, with the deep learning algorithm, a sepsis status of the individual patient based on the: (i) observation data of the individual patient, and (ii) history data of the individual patient.

OTHER MATTERS

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

What is claimed:

1. A computer-implemented method for predicting a work-status of an individual patient, the method comprising, via one or more processors:
   receiving, by the one or more processors, observation data and historical work-statuses of the individual patient, wherein the observation data is represented by an input observation matrix and the historical work-statuses are represented by a work-statuses matrix; and
   training, by the one or more processors, a machine learning algorithm to predict work status based on (i) observation data and (ii) historical work-statuses, wherein training the machine learning algorithm includes:
      transforming the input observation matrix to lower dimensional vectors;
      inputting, into the machine learning algorithm, the lower dimensional vectors;
      predicting, with the machine learning algorithm, a work-status of the individual patient following a predetermined time period based on the observation data of the individual patient;
      splitting the work-status into a training dataset and a validation dataset;
      filtering and normalizing the training dataset to minimize information leakage;
      validating the machine learning algorithm by comparing the predicted work-status with the validation dataset; and
      dynamically updating the machine learning algorithm using the training dataset.

2. The computer-implemented method of claim 1, wherein the observation data includes data of diagnoses, treatments, patient outcomes, and medications.

3. The computer-implemented method of claim 1, wherein:
   the observation data, and the historical work-statuses each include a plurality of timesteps; and
   the prediction of the work-status of the individual patient is made at each timestep of the plurality of timesteps.

4. The computer-implemented method of claim 1, wherein the prediction of the work-status of the individual patient is made as a probability.

5. The computer-implemented method of claim 1, wherein:
   the observation data includes: (i) a plurality of timesteps, and (ii) feature data; and
   the feature data includes: (i) dynamic data that changes between two timesteps of the plurality of timesteps, and (ii) static data that remains constant across all timesteps of the plurality of timesteps.

6. The computer-implemented method of claim 1, wherein the observation data includes feature data, and wherein the feature data includes:
   an age of an input patient;
   a gender of the input patient;
   an occupation of the input patient;
   a diagnosis of the input patient;
   a treatment of the input patient;
   a diagnosis accompanying the treatment;
   a medication of the input patient, and dispense amount of the medication; and
   a health status of the input patient.

7. The computer-implemented method of claim 1, wherein:
   the observation data includes a low dimension category feature including one of gender data or health status data;
   the observation data further includes a high dimension category feature including one of occupation data, diagnosis data, treatment data, or medication data; and
   the computer-implemented method further includes:
      converting the low dimension category feature to a one-hot-encoding vector, and aggregating values of the one-hot-encoding vector; and
      mapping the high dimension category feature to a real-space vector with a dimension proportional to a number of category values of the high dimension category feature.

8. The computer-implemented method of claim 1, wherein training the machine learning algorithm further includes:
   using an objective function to minimize binary-cross entropy between a vector of the observation data and a vector of the historical work-statuses; and using a special generator function to pad variable lengths of the observation data.

9. The computer-implemented method of claim 1, wherein:
input observations of the observation data are represented by $X_{n,t}$; and
the historical work-statuses are represented as binary health-state variables represented by $Y_{n,t}$.

10. A computer system for predicting a work-status of an individual patient, the computer system comprising one or more processors configured to:
receive observation data and historical work-statuses of the individual patient, wherein the observation data is represented by an input observation matrix and the historical work-statuses are represented by a work-statuses matrix; and
train a machine learning algorithm to predict work status based on (i) observation data and (ii) historical work-statuses, wherein training the machine learning algorithm includes:
transform the input observation matrix to lower dimensional vectors;
input, into the machine learning algorithm, the lower dimensional vectors;
predict, with the machine learning algorithm, the work-status of the individual patient following a predetermined time period based on the observation data of the individual patient;
split the work-status into a training dataset and a validation dataset;
filter and normalize the training dataset to minimize information leakage;
validate the machine learning algorithm by comparing the predicted work-status with the validation dataset; and
dynamically update the machine learning algorithm using the training dataset.

11. The computer system of claim 10, wherein the observation data includes data of diagnoses, treatments, and medications.

12. The computer system of claim 10, wherein:
the observation data includes: (i) a plurality of timesteps, and (ii) feature data; and
the feature data includes: (i) dynamic data that changes between two timesteps of the plurality of timesteps, and (ii) static data that remains constant across all timesteps of the plurality of timesteps.

13. A computer device for predicting a work-status of an individual patient, the computer device comprising:
one or more processors; and
one or more memories coupled to the one or more processors;
the one or more memories including computer executable instructions stored therein that, when executed by the one or more processors, cause the one or more processors to:
receive observation data and historical work-statuses of the individual patient, wherein the observation data is represented by an input observation matrix and the historical work-statuses are represented by a work-statuses matrix; and
train a machine learning algorithm to predict work status based on (i) observation data and (ii) historical work-statuses, wherein training the machine learning algorithm includes:
transform the input observation matrix to lower dimensional vectors;
input, into the machine learning algorithm, the lower dimensional vectors;
predict, with the machine learning algorithm, a work-status of the individual patient following a predetermined time period based on the observation data of the individual patient;
split the work-status into a training dataset and a validation dataset;
filter and normalize the training dataset to minimize information leakage;
validate the machine learning algorithm by comparing the predicted work-status with the validation dataset; and
dynamically update the machine learning algorithm using the training dataset.

14. The computer device of claim 13, wherein the observation data includes data of diagnoses, treatments, and medications.

15. The computer device of claim 13, wherein the machine learning algorithm is a deep learning algorithm.

* * * * *